United States Patent
Koyama

(10) Patent No.: US 8,508,360 B2
(45) Date of Patent: Aug. 13, 2013

(54) WIRELESS SENSOR DEVICE

(75) Inventor: Jun Koyama, Sagamihara (JP)

(73) Assignee: Semiconductor Energy Laboratory Co., Ltd., Atsugi-shi, Kanagawa-ken (JP)

( * ) Notice: Subject to any disclaimer, the term of this patent is extended or adjusted under 35 U.S.C. 154(b) by 0 days.

(21) Appl. No.: 13/558,373

(22) Filed: Jul. 26, 2012

(65) Prior Publication Data

US 2012/0287584 A1 Nov. 15, 2012

Related U.S. Application Data

(63) Continuation of application No. 13/118,872, filed on May 31, 2011, now Pat. No. 8,242,903, which is a continuation of application No. 11/902,718, filed on Sep. 25, 2007, now Pat. No. 7,965,180.

(30) Foreign Application Priority Data

Sep. 28, 2006 (JP) .................................. 2006-263752

(51) Int. Cl.
G08B 1/08 (2006.01)

(52) U.S. Cl.
USPC .................................. 340/539.12; 340/572.1

(58) Field of Classification Search
USPC ............. 340/539.12, 572.1, 870.01; 600/300
See application file for complete search history.

(56) References Cited

U.S. PATENT DOCUMENTS

| | | | |
|---|---|---|---|
| 6,229,444 B1 | 5/2001 | Endo et al. | |
| 6,285,284 B1 | 9/2001 | Soe et al. | |
| 6,585,166 B1 | 7/2003 | Ookawa et al. | |
| 6,770,176 B2 | 8/2004 | Benson et al. | |
| 6,985,088 B2 | 1/2006 | Goetz et al. | |
| 7,478,108 B2 | 1/2009 | Townsend et al. | |
| 7,604,591 B2 | 10/2009 | Uchiyama et al. | |
| 7,622,736 B2 | 11/2009 | Moriya et al. | |
| 7,663,473 B2 | 2/2010 | Koyama | |
| 7,710,270 B2 | 5/2010 | Shionoiri et al. | |
| 7,743,151 B2 | 6/2010 | Vallapureddy et al. | |
| 7,768,391 B2 | 8/2010 | Koyama et al. | |
| 7,786,867 B2 | 8/2010 | Hamel et al. | |
| 7,791,012 B2 | 9/2010 | Hirose | |
| 7,928,910 B2 | 4/2011 | Suzuki et al. | |
| 7,965,180 B2 | 6/2011 | Koyama | |
| 8,242,903 B2 * | 8/2012 | Koyama | 340/539.12 |
| 2004/0193020 A1 | 9/2004 | Chiba et al. | |
| 2006/0267769 A1 | 11/2006 | Ito et al. | |

(Continued)

FOREIGN PATENT DOCUMENTS

| | | |
|---|---|---|
| EP | 1 681 010 A | 7/2006 |
| JP | 05-291991 A | 11/1993 |

(Continued)

*Primary Examiner* — John A Tweel, Jr.

(74) *Attorney, Agent, or Firm* — Eric J. Robinson; Robinson Intellectual Property Law Office, P.C.

(57) ABSTRACT

A wireless sensor device capable of constant operation without replacement of batteries. The wireless sensor device is equipped with a rechargeable battery and the battery is recharged wirelessly. Radio waves received at an antenna circuit are converted into electrical energy and stored in the battery. A sensor circuit operates with the electrical energy stored in the battery, and acquires information. Then, a signal containing the information acquired is converted into radio waves at the antenna circuit, whereby the information can be read out wirelessly.

21 Claims, 23 Drawing Sheets

(56) References Cited

U.S. PATENT DOCUMENTS

| | | |
|---|---|---|
| 2007/0229228 A1 | 10/2007 | Yamazaki et al. |
| 2007/0229279 A1 | 10/2007 | Yamazaki et al. |
| 2007/0278998 A1 | 12/2007 | Koyama |
| 2007/0285246 A1 | 12/2007 | Koyama |
| 2008/0055047 A1 | 3/2008 | Osada et al. |
| 2008/0055279 A1 | 3/2008 | Osada et al. |
| 2008/0058029 A1 | 3/2008 | Sato et al. |
| 2008/0060422 A1 | 3/2008 | Hosoya |
| 2008/0210762 A1 | 9/2008 | Osada et al. |

FOREIGN PATENT DOCUMENTS

| | | |
|---|---|---|
| JP | 08-010232 | 1/1996 |
| JP | 2001-224551 A | 8/2001 |
| JP | 2001-231186 | 8/2001 |
| JP | 2003-255877 A | 9/2003 |
| JP | 2003-315209 A | 11/2003 |
| JP | 2004-121632 | 4/2004 |
| JP | 3591348 | 9/2004 |
| JP | 3591348 | 11/2004 |
| JP | 2005-080933 A | 3/2005 |
| JP | 2005-125010 A | 5/2005 |
| JP | 2006-099757 | 4/2006 |
| WO | WO-01/01340 | 1/2001 |
| WO | WO 2006/025594 | 3/2006 |

* cited by examiner

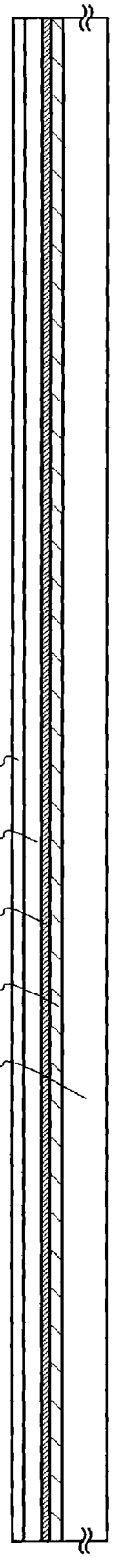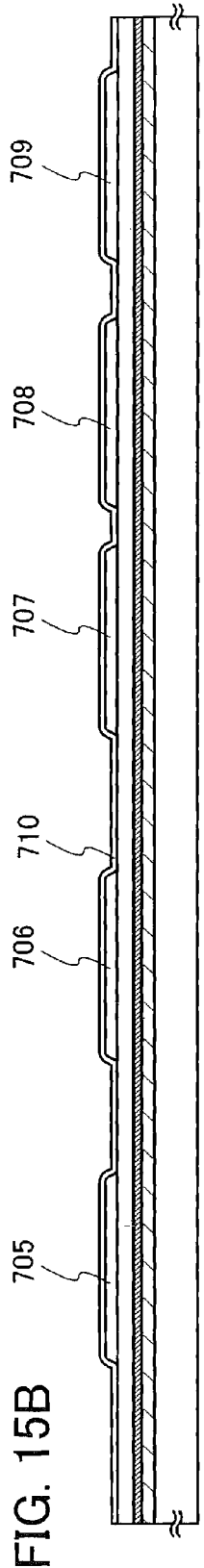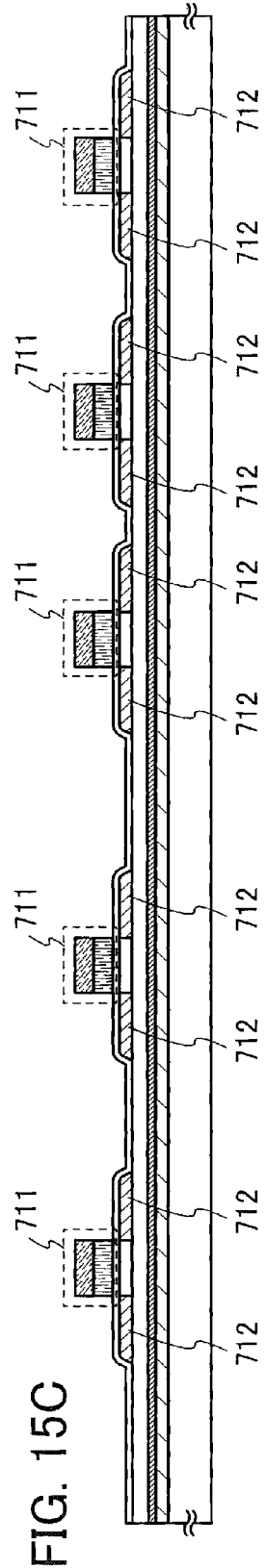

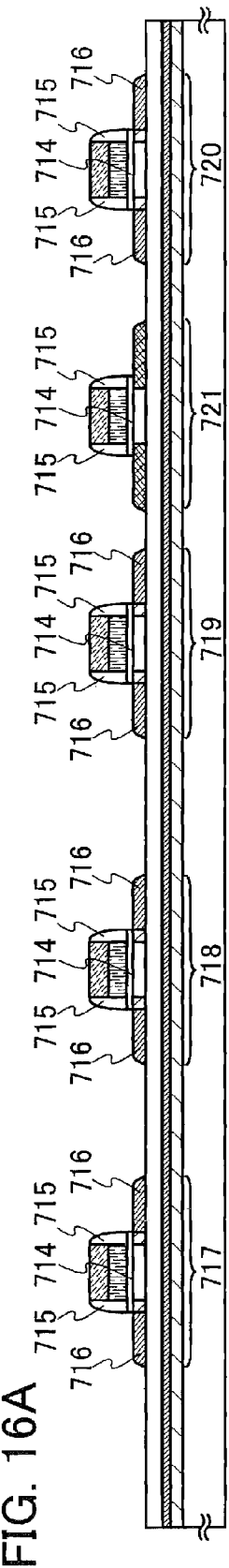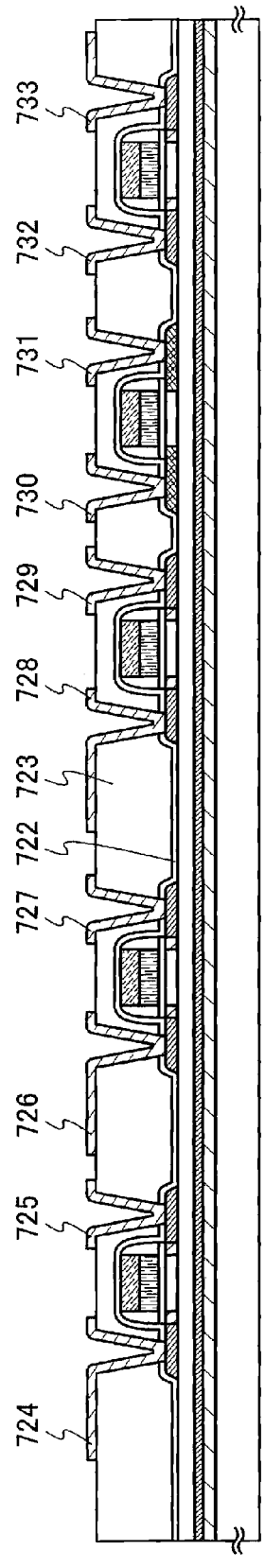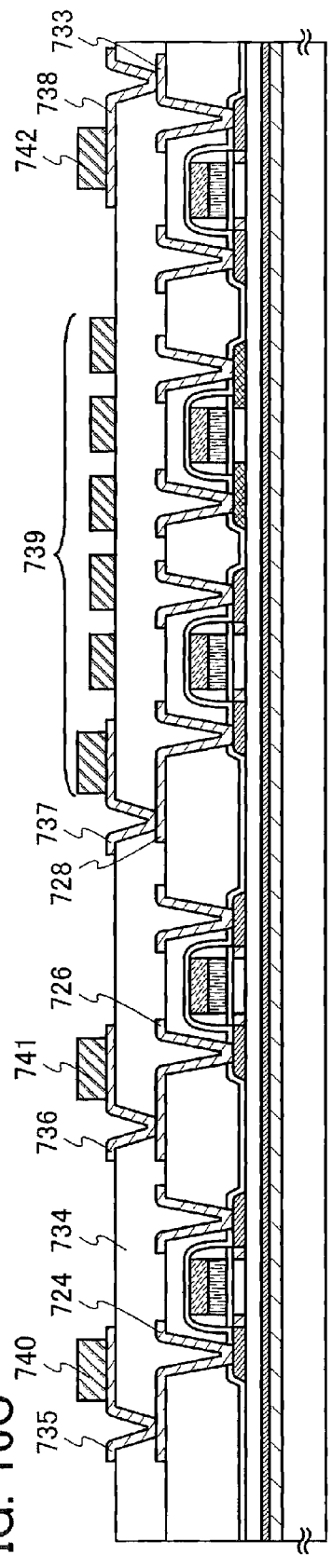

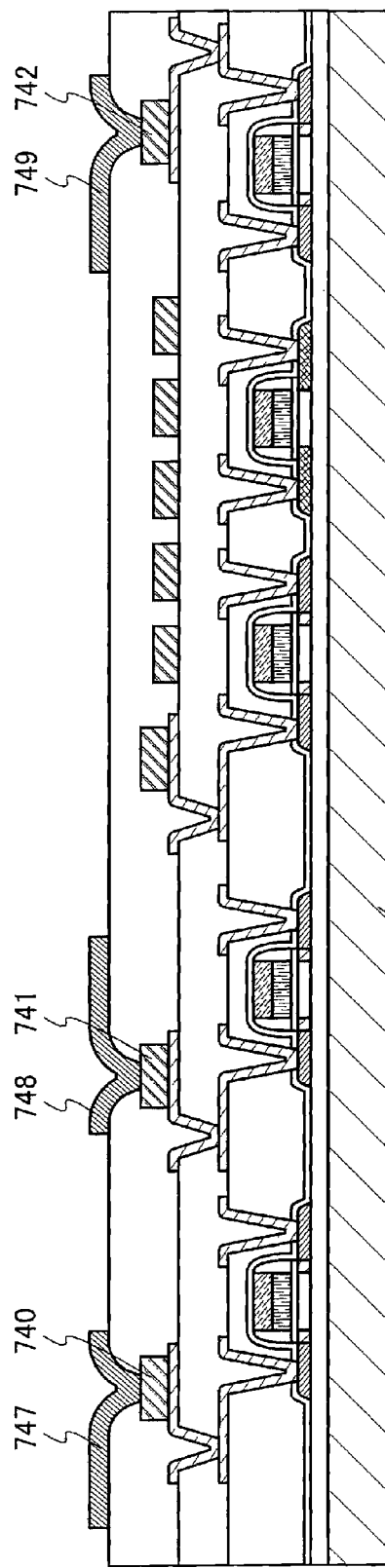
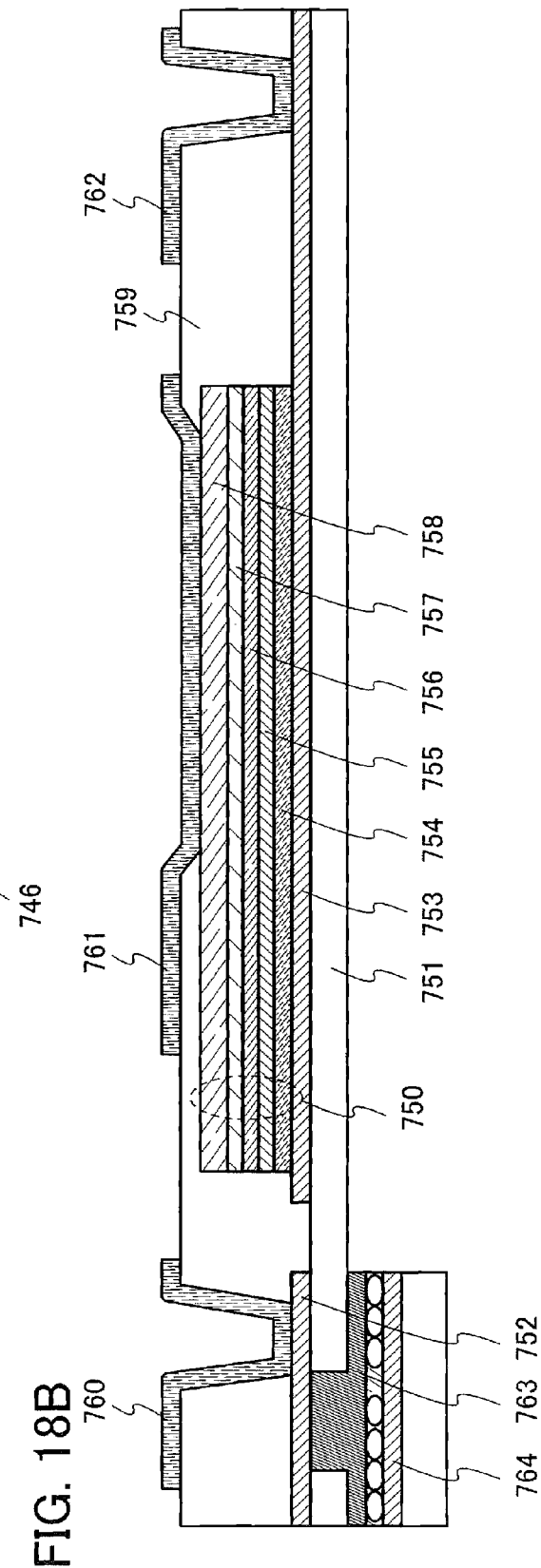
FIG. 18A
FIG. 18B

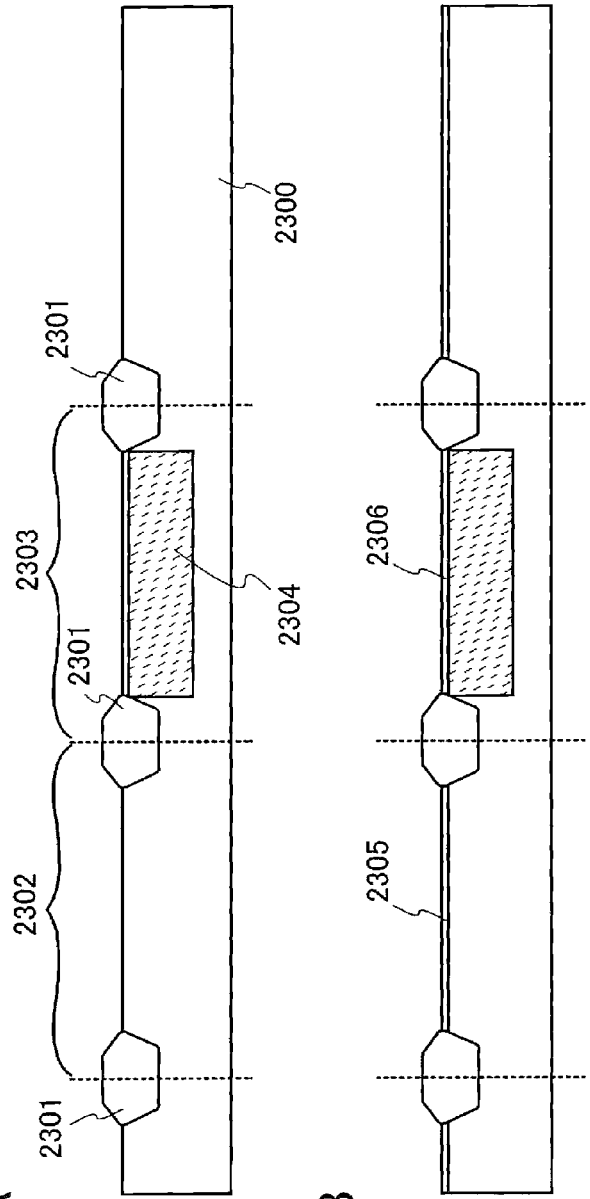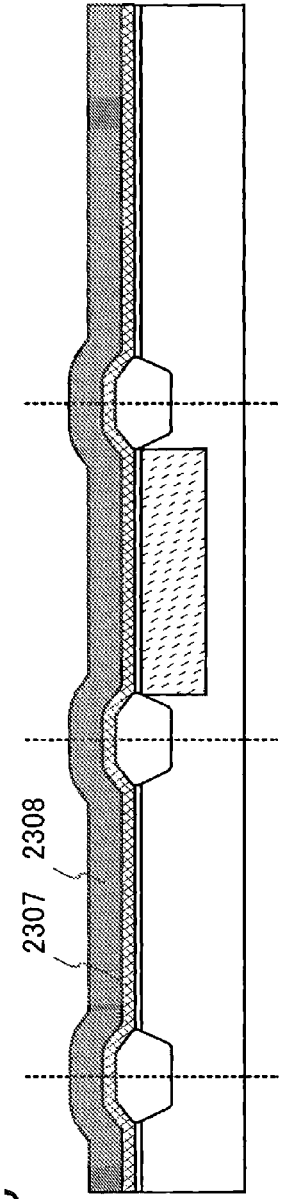

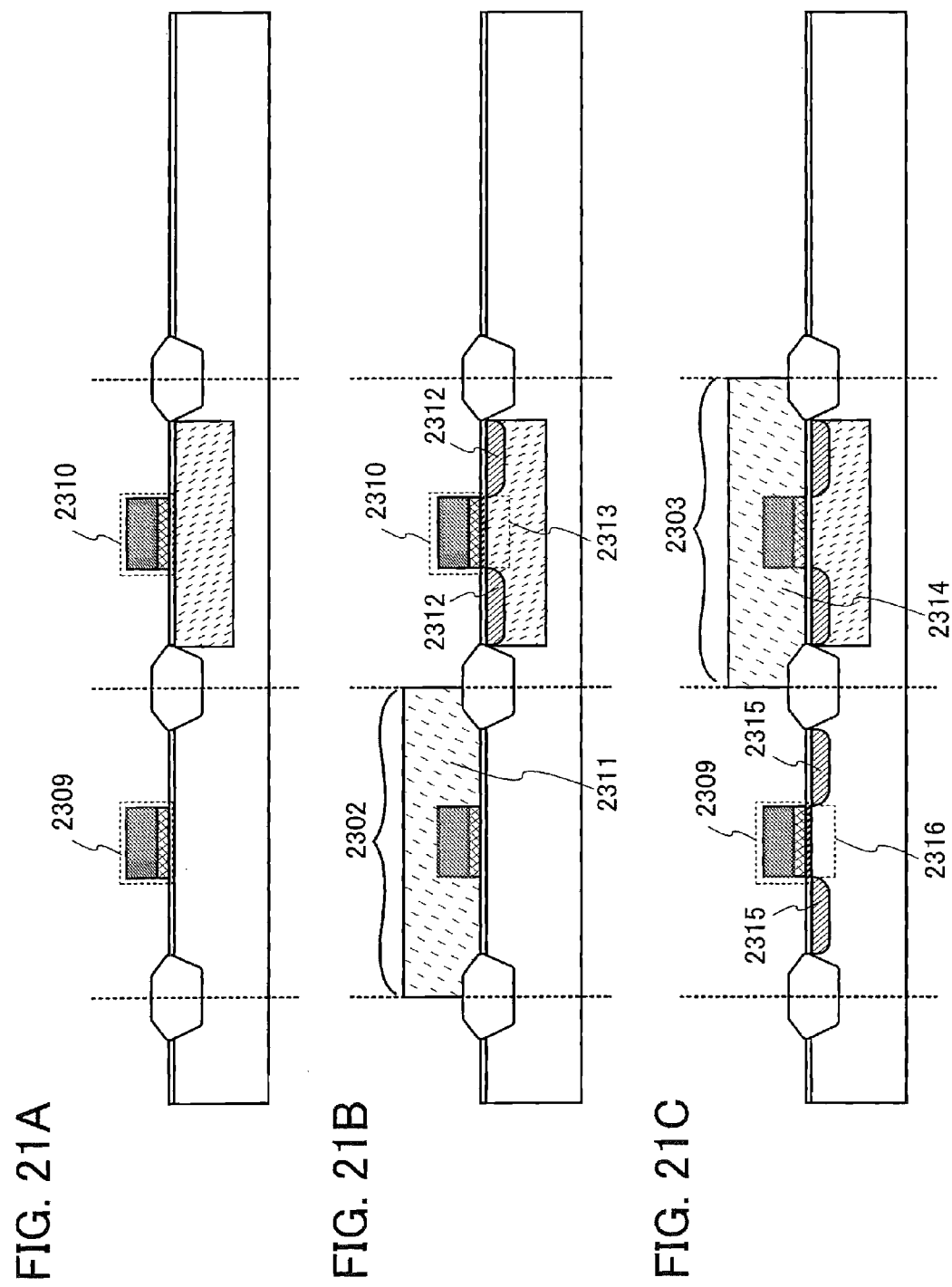

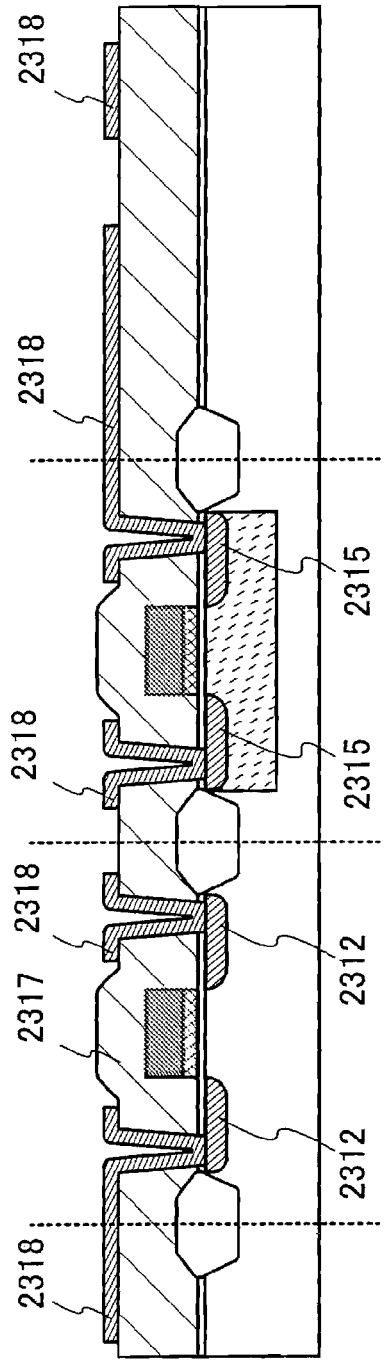
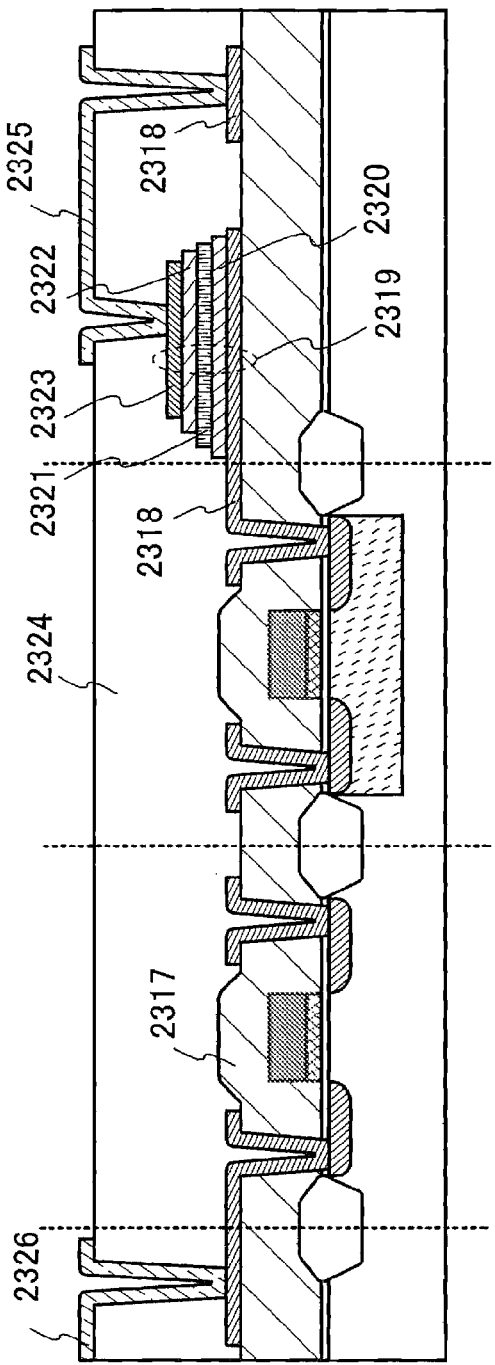

WIRELESS SENSOR DEVICE

BACKGROUND OF THE INVENTION

1. Field of the Invention

The present invention relates to a wireless sensor device having a so-called sensing function, which is capable of reading out information without contact, e.g., by radio communication. In particular, the invention relates to a wireless sensor device which is used while being implanted in, swallowed by, or attached to the living body.

2. Description of the Related Art

Nowadays, an increasing number of information is being processed with the development of IT technology. Among them is the information management for human health. For example, health checkups are regularly conducted at companies, schools, and the like; individuals are informed of their heath conditions at least once or twice a year. When the condition of one's health is not good, he/she will be noticed of the fact and receives treatment at a hospital.

Also, simple health measurement instruments for domestic use have been developed for easy checkups of one's health conditions. In recent years, portable measurement instruments have also become widespread, contributing to early detection of diseases.

Reference 1 (Japanese Published Patent Application No. 2004-121632) is one of the examples of the heath measurement instrument.

Reference 1 discloses a portable blood-pressure measurement instrument. Using such a measurement instrument, one can easily know his/her health condition.

However, the conventional health measurement instrument disclosed in Reference 1 has the following problems: even though the size of the health measurement instrument is reduced to some extent, it is still large for being carried around. Moreover, even when a user acquires information with the measurement instrument, he/she may be unconscious of a change in physical condition because the information cannot be immediately seen by a medical specialist. This could result in a progression of disease.

In view of the foregoing, a semiconductor device having a function of wirelessly acquiring physical information has been devised, for example by attaching a sensor device having a radio function to a human body. A specific example thereof is disclosed in Reference 2 (Japanese Published Patent Application No. 2006-99757). In this example, physical information in particular can be acquired with a dedicated wireless reader device without the help of medical institutions and the like.

SUMMARY OF THE INVENTION

However, the wireless sensor device disclosed in Reference 2 is a passive type and operates only when there is a wireless signal supply from outside. Thus, the wireless sensor device cannot operate when there is no wireless signal supply from outside. Therefore, this device is not effective in constantly acquiring physical information.

Meanwhile, the above-described problems can be solved by forming the wireless sensor device to be an active device and building a battery into the device. However, when the wireless sensor device is implanted in or swallowed by the body, the battery cannot be replaced easily. Furthermore, there is another problem in that the wireless sensor device becomes inactive when the battery runs out of charge.

In view of the foregoing problems, it is an object of the invention to provide a wireless sensor device capable of constant operation without replacement of batteries.

According to the invention, a wireless sensor device is equipped with a rechargeable battery and the battery is recharged wirelessly. Specifically, the wireless sensor device of the invention includes an antenna circuit for transmission and reception of radio waves, a battery for storing electrical energy obtained from the radio waves, and a sensor circuit for acquiring (sensing) information.

Radio waves received at the antenna circuit are converted into electrical energy, and the electrical energy is stored in the battery. The sensor circuit operates with the electrical energy stored in the battery, and acquires information. Then, a signal containing the information acquired is converted into radio waves at the antenna circuit, whereby the information can be read out wirelessly.

Note that a memory circuit may be used to temporarily store the information acquired. In that case, by converting the information stored in the memory circuit into radio waves at the antenna circuit, the information can be read out wirelessly.

In the case of using the wireless sensor device of the invention in the living body, radio waves transmitted from outside of the body are converted into electrical energy at the antenna circuit so that the electrical energy is stored in the battery. The sensor circuit operates with the electrical energy stored in the battery, and acquires physical information. Physical information means information that can serve as an indicator of the health condition of the living body. Typical examples of physical information include blood pressure, heart rate, body temperature, respiration rate, the amount of gas in the blood, the value of action current such as an electrocardiogram or an electroencephalogram, blood glucose level, an internal image of the body, and the like.

It is acceptable as long as a sensor used for the sensor circuit is selected in accordance with the physical information to be acquired. Further, by providing a plurality of sensor circuits in a wireless sensor device, a plurality of kinds of physical information can be acquired.

The physical information acquired is stored in the memory circuit. Then, by converting the physical information stored in the memory circuit into radio waves at the antenna circuit, the physical information can be read out wirelessly.

The wireless sensor device of the invention can be used not only for acquisition of physical information of the living body, but also for constant acquisition of information in areas where it is difficult to acquire information by contact.

As described above, according to the invention, a wireless sensor device can be supplied with electrical energy without contact. Therefore, replacement of batteries is not necessary.

In the case of using the wireless sensor device in the living body, the battery can be recharged without contact, without hurting the living body, while the wireless sensor device is being placed in the living body. By using electricity stored in the battery, the wireless sensor device of the invention can constantly acquire physical information.

Physical information acquired by the wireless sensor device can be transmitted wirelessly. Therefore, the physical information can be managed with IT technology to be utilized for early detection or treatment of diseases and the like.

The wireless sensor device of the invention can be widely used as a device that can constantly acquire information not only in the living body but also in areas where it is difficult to acquire information by contact. For example, the wireless sensor device can be utilized for sensing in areas where access of humans is limited such as a radiation controlled area.

BRIEF DESCRIPTION OF THE DRAWINGS

In the accompanying drawings:

FIGS. 15A to 15D illustrate a method of fabricating a wireless sensor device of the invention;

FIGS. 16A to 16C illustrate a method of fabricating a wireless sensor device of the invention;

FIGS. 18A and 18B illustrate a method of fabricating a wireless sensor device of the invention;

FIGS. 20A to 20C illustrate a method of fabricating a wireless sensor device of the invention;

FIGS. 21A to 21C illustrate a method of fabricating a wireless sensor device of the invention;

FIGS. 22A and 22B illustrate a method of fabricating a wireless sensor device of the invention.

DETAILED DESCRIPTION OF THE INVENTION

Figure 1:
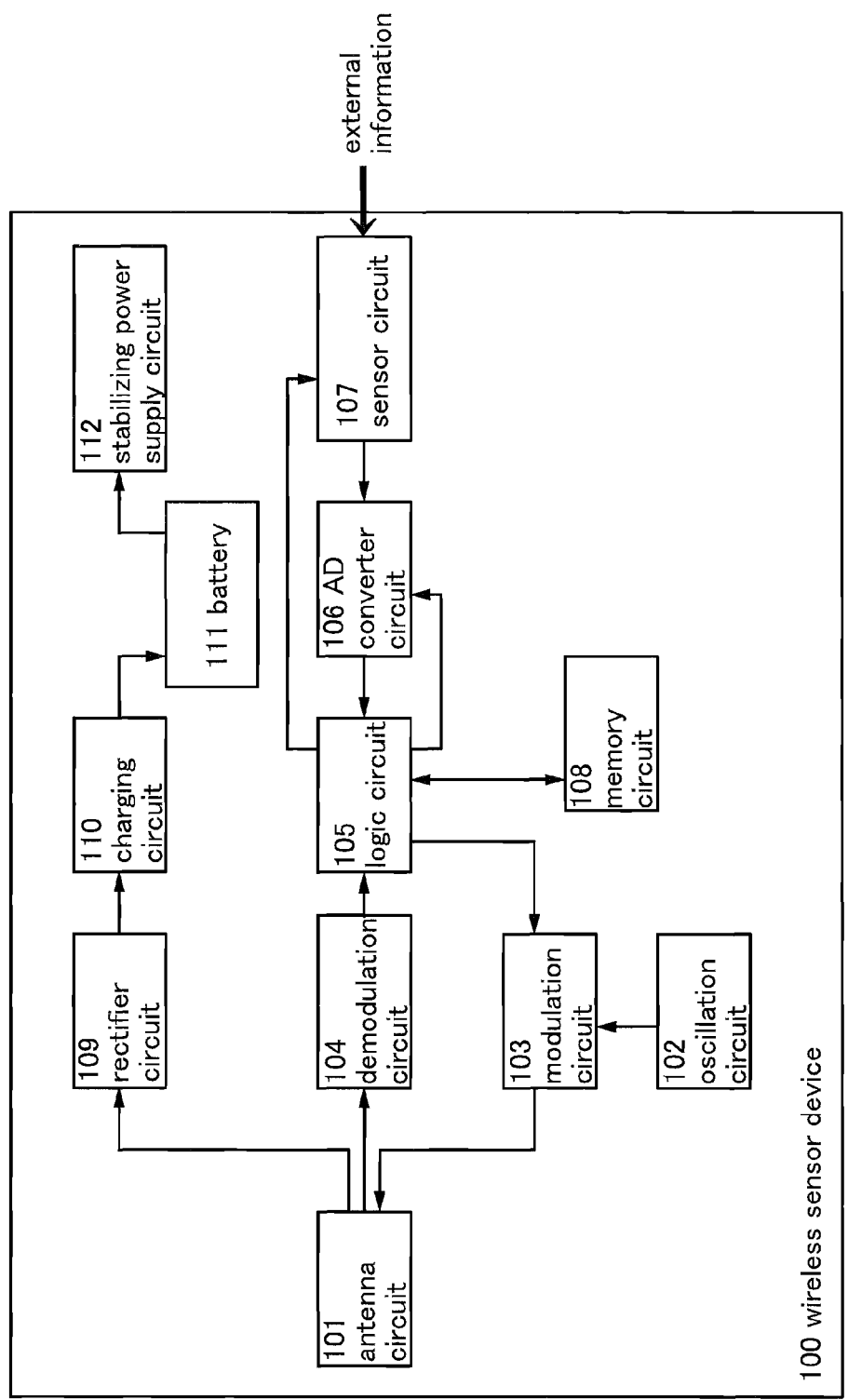
FIG. 1 is a block diagram illustrating the configuration of a wireless sensor device of the invention.

Embodiment modes and embodiments of the invention will be hereinafter described with reference to the accompanying drawings. Note that the invention can be implemented in various different ways and it will be easily understood by those skilled in the art that various changes and modifications can be made in the invention without departing from the spirit and scope thereof. Therefore, the invention should not be construed as being limited to the description in the following embodiment modes and embodiments. In the accompanying drawings, like portions or portions having like functions are denoted by like reference numerals, and repetitive description thereof will be omitted.

Embodiment Mode 1

Embodiment Mode 1 of the invention is shown in FIG. 1. FIG. 1 illustrates a block diagram of the invention. A wireless sensor device 100 includes an antenna circuit 101, an oscillation circuit 102, a modulation circuit 103, a demodulation circuit 104, a logic circuit 105, an AD converter circuit 106, a sensor circuit 107, a memory circuit 108, a rectifier circuit 109, a charging circuit 110, a battery 111, and a stabilizing power supply circuit 112.

Figure 3A:
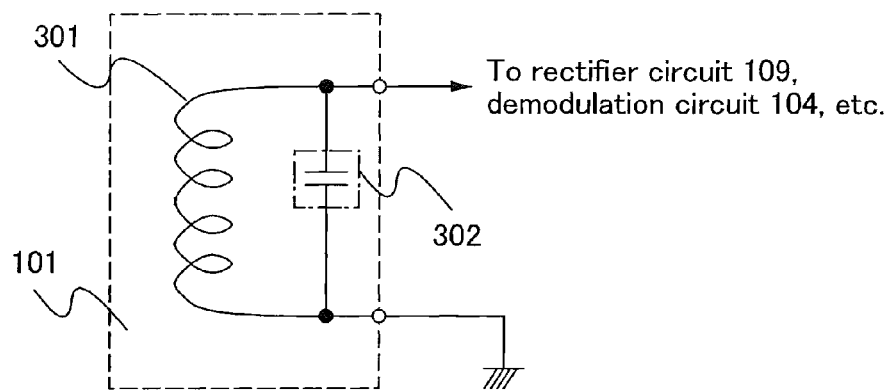
FIGS. 3A and 3B are block diagrams illustrating the configurations of an antenna circuit and a rectifier circuit, respectively, of a wireless sensor device of the invention.
Figure 3B:
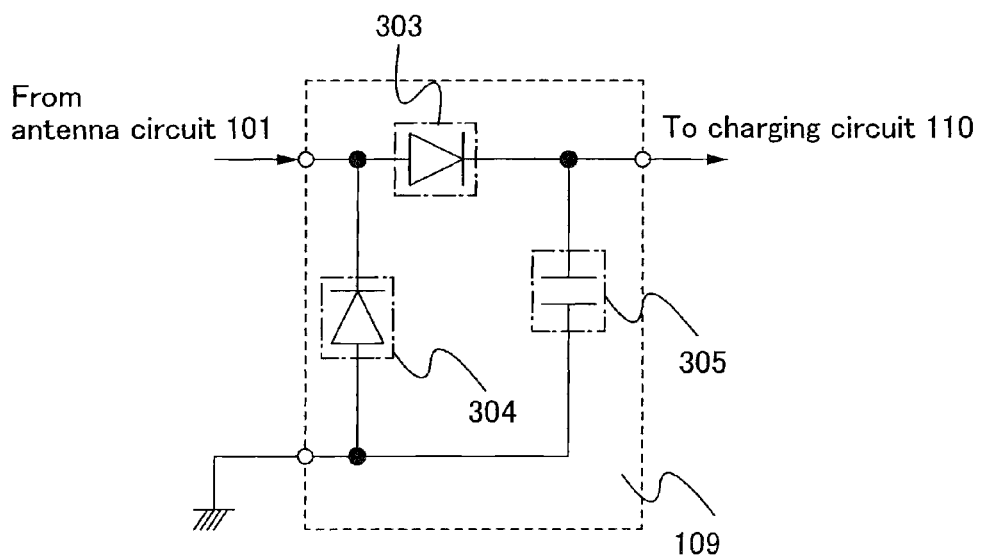

In the case of performing communication with a magnetic field, the antenna circuit 101 includes, as shown in FIG. 3A, a coiled antenna 301 and a tuning capacitor 302. The rectifier circuit 109 includes, as shown in FIG. 3B, a diode 303, a diode 304, and a smoothing capacitor 305. However, the configurations of the antenna circuit 101 and the rectifier circuit 109 are not limited to them. In the case of performing communication with not a magnetic field but an electric field, the antenna does not need to be in a coiled form.

The operation of the wireless sensor device 100 in this embodiment mode will now be described. An AC signal received at the antenna circuit 101 is half-wave rectified by the diodes 303 and 304, and then smoothed by the smoothing capacitor 305. By this smoothed voltage, the charging circuit 110 is activated to charge the battery 111. As the battery 111, for example, a secondary battery, a high-capacity capacitor, or the like can be used.

An output voltage of the battery 111 is stabilized by the stabilizing power supply circuit 112, and the stabilized voltage is supplied to the oscillation circuit 102, the modulation circuit 103, the demodulation circuit 104, the logic circuit 105, the AD converter circuit 106, the sensor circuit 107, and the memory circuit 108.

Signals communicated with an external device are transmitted through carrier modulation. Therefore, the wireless sensor device of the invention should demodulate the modulated signals. Examples of the carrier frequency include, but not limited to, 125 kHz, 13.56 MHz, 950 MHz, and the like. In addition, examples of a modulation method include, but not limited to, amplitude modulation, frequency modulation, phase modulation, and the like.

Upon input of an external radio wave, which is a signal requesting to activate the sensor circuit 107, to the antenna circuit 101, the signal is demodulated by the demodulation circuit 104. The demodulated signal is processed by the logic circuit 105. When the input signal is an encoded signal, it is decoded in the logic circuit 105. For example, when the signal from the external transmitter has been encoded with modified Miller codes, NRZ-L codes, or the like, the encoded signal is decoded in the logic circuit 105. The decoded data is transmitted to the AD converter circuit 106 and the sensor circuit 107, whereby the AD converter circuit 106 and the sensor circuit 107 are activated.

With the activated sensor circuit 107, the wireless sensor device 100 can detect external information. External information herein includes, but not limited to, pressure, light, odor, sound, and the like. The sensor circuit 107 has a function of converting such external information into an electrical signal. The output of the sensor circuit 107 is converted into a digital signal by the AD converter circuit 106. The output signal of the AD converter circuit 106 is processed by the logic circuit 105. For example, the signal is encoded by the logic circuit 105 when necessary. The output of the logic circuit 105 is modulated by the modulation circuit 103 and then input to the antenna circuit 101. The modulation circuit 103 performs modulation by mixing the output of the oscillation circuit 102 and the output of the logic circuit 105. The signal input to the antenna circuit 101 is radiated as radio waves.

As the sensor circuit 107, for example, a pressure sensor, a photosensor, an odor sensor, a sound sensor, and the like can be used, but the invention is not limited to these. The memory circuit 108 is used for storing information that has been sensed, and is preferably nonvolatile memory, but the invention is not limited to this. Even when the memory circuit 108 is volatile memory, it can function in the same way as nonvolatile memory as long as it can secure a power supply. The memory circuit 108 can be, for example, SRAM, DRAM, flash memory, EEPROM, FeRAM, or the like.

Figure 2:
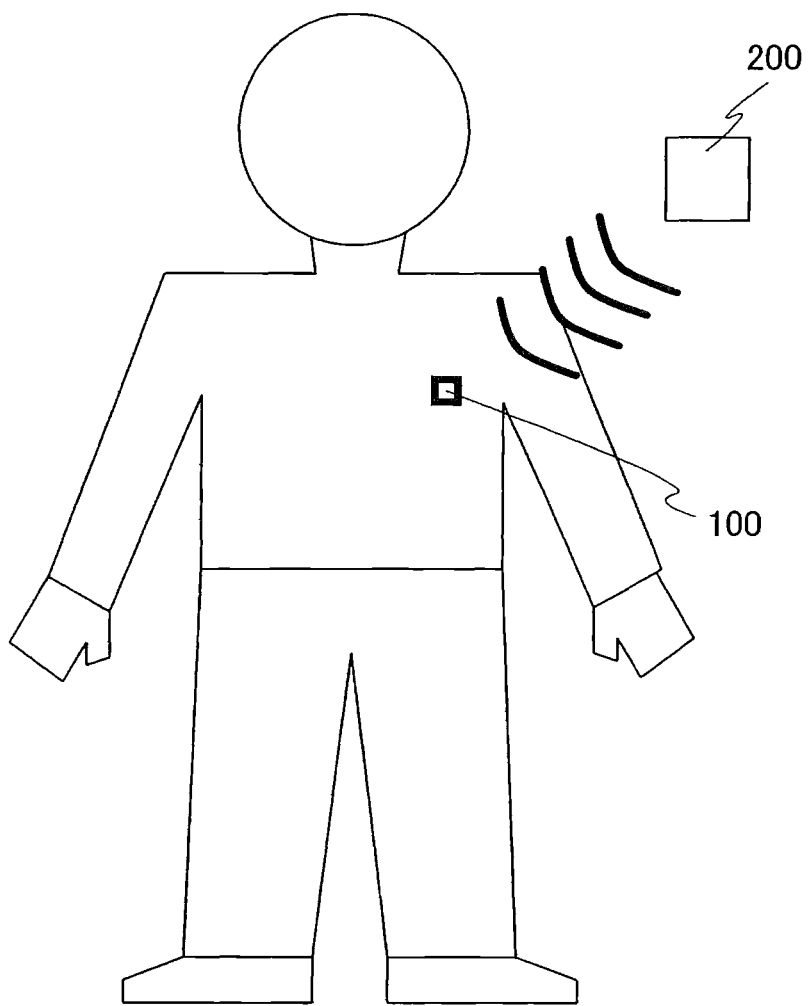
FIG. 2 illustrates application of the invention to a human body.

A physical information acquisition system that uses the wireless sensor device of the invention will be briefly described with reference to FIG. 2. FIG. 2 is a schematic view of a physical information acquisition system that obtains physical information of humans without contact. The wireless sensor device 100 is placed inside the living body. Specifically, the wireless sensor device 100 may be either implanted in the living body or swallowed by the living body so as to be placed in a digestive organ. The battery included in the wireless sensor device of the invention can, even when placed inside the living body, store electrical energy without contact with the use of radio waves.

Note that the wireless sensor device of the invention may be configured such that the battery is charged not only in sensing operation but constantly, i.e., even when sensing operation is not conducted. With such a configuration, power that will be consumed for one sensing operation can be surely secured by the battery even under the condition of weak radio waves.

The use of the wireless sensor device of the invention is not limited to the use inside the living body. That is, the wireless sensor device of the invention can also be used while being attached to the surface of the living body.

Radio waves are transmitted from an interrogator 200 to the wireless sensor device 100. Upon reception of the radio waves, the wireless sensor device 100 sends physical information, which has been acquired by the sensor circuit 107 included in the wireless sensor device 100, back to the interrogator 200. The interrogator 200 is connected to an information system (not shown) which analyzes the physical information acquired. In this manner, physical information of humans can be acquired without carrying a bulky measurement instrument. Further, since information can be analyzed automatically, it is possible to prevent progression of disease, which would otherwise be caused by delay of notification.

Embodiment Mode 2

Figure 4:
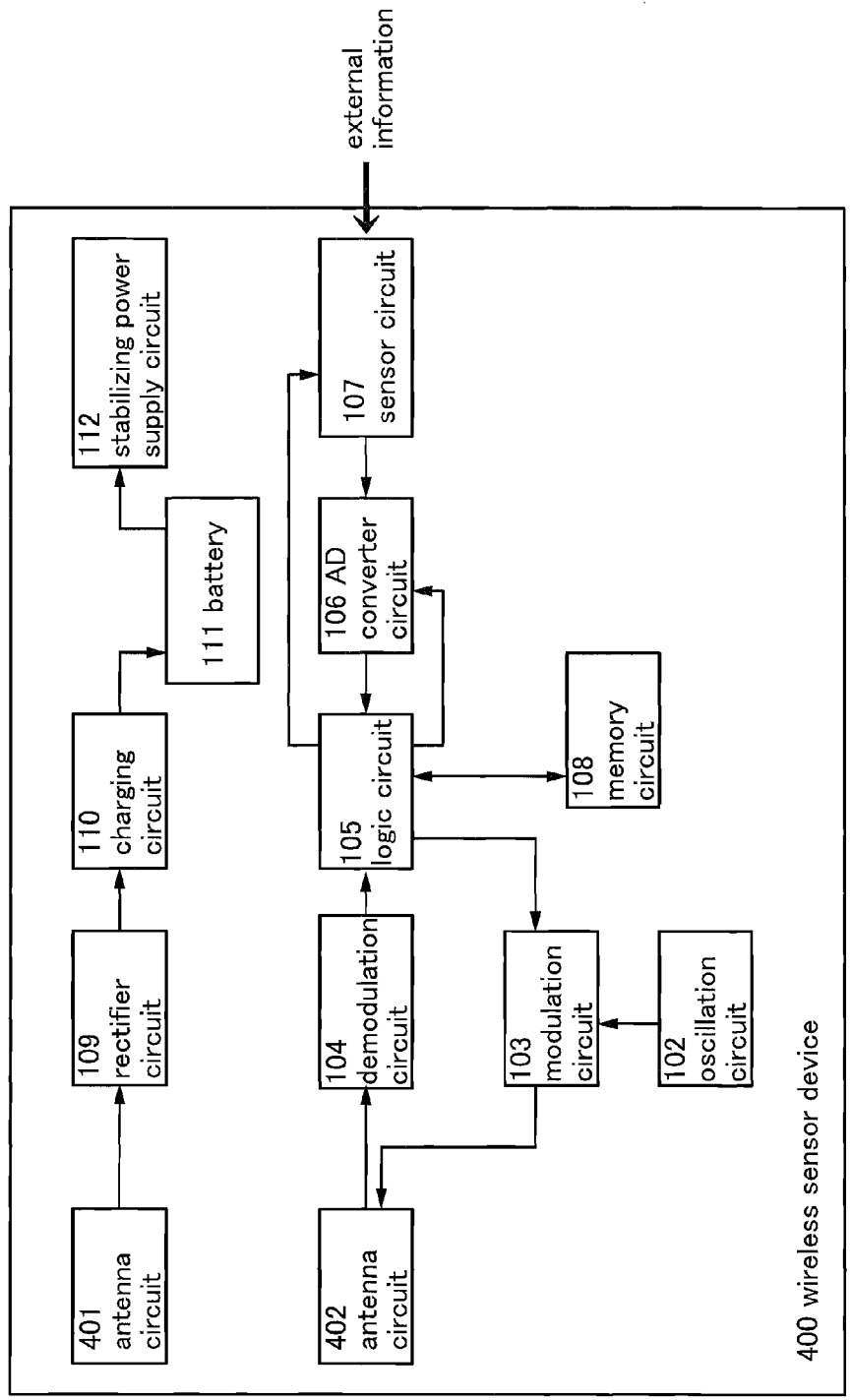
FIG. 4 is a block diagram illustrating the configuration of a wireless sensor device of the invention.

Embodiment Mode 2 of the invention is shown in FIG. 4. FIG. 4 illustrates a block diagram of the invention. A wireless sensor device 400 includes antenna circuits 401 and 402, the oscillation circuit 102, the modulation circuit 103, the demodulation circuit 104, the logic circuit 105, the AD converter circuit 106, the sensor circuit 107, the memory circuit 108, the rectifier circuit 109, the charging circuit 110, the battery 111, and the stabilizing power supply circuit 112.

In this embodiment mode, the antenna circuit 401 for reception of power and the antenna circuit 402 for reception of signals are provided, unlike Embodiment Mode 1. When a plurality of antenna circuits having different functions are selectively used in this manner, power transmission and signal transmission can be conducted by using different radio frequencies. For example, power transmission can be conducted with radio waves having a frequency of 13.56 MHz by utilizing a magnetic field, while signal transmission can be conducted with radio waves having a frequency of 950 MHz by utilizing an electric field. By selectively using a magnetic field and an electric field in accordance with the frequency, power can be transmitted only a short distance, while signal can be transmitted both short and long distances. If power transmission is conducted with a radio frequency of 950 MHz, there is a possibility that high power is transmitted to a far place, which could cause interference with signal reception of other wireless devices. Therefore, when the distance of power transmission can be short, it is preferable to lower the frequency and use a magnetic field.

The operation of the wireless sensor device 400 in this embodiment mode will now be described. An AC signal received at the antenna circuit 401 is half-wave rectified by the diodes 303 and 304 shown in FIG. 3B, and then smoothed by the smoothing capacitor 305. By this smoothed voltage, the charging circuit 110 is activated to charge the battery 111. As the battery 111, for example, a secondary battery, a high-capacity capacitor, or the like can be used.

An output voltage of the battery 111 is stabilized by the stabilizing power supply circuit 112, and the stabilized voltage is supplied to the oscillation circuit 102, the modulation circuit 103, the demodulation circuit 104, the logic circuit 105, the AD converter circuit 106, the sensor circuit 107, and the memory circuit 108.

Signals communicated with an external device are transmitted through carrier modulation. Therefore, the wireless sensor device of the invention should demodulate the modulated signal. Examples of the carrier frequency include, but not limited to, 125 kHz, 13.56 MHz, 950 MHz, and the like. In addition, examples of a modulation method include, but not limited to, amplitude modulation, frequency modulation, phase modulation, and the like.

A signal input to the antenna circuit 402 is demodulated in the demodulation circuit 104. The demodulated signal is processed in the logic circuit 105. When the input signal is an encoded signal, it is decoded in the logic circuit 105. For example, when the signal from the external transmitter has been encoded with modified Miller codes, NRZ-L codes, or the like, the encoded signal is decoded in the logic circuit 105. The decoded data is transmitted to the AD converter circuit 106 and the sensor circuit 107, whereby the AD converter circuit 106 and the sensor circuit 107 are activated.

With the activated sensor circuit 107, the wireless sensor device 400 can detect external information. External information herein includes, but not limited to, pressure, light, odor, sound, and the like. The sensor circuit 107 has a function of converting such external information into an electrical signal. The output of the sensor circuit 107 is converted into a digital signal by the AD converter circuit 106. The output signal of the AD converter circuit 106 is processed by the logic circuit 105. For example, the signal is encoded by the logic circuit 105 when necessary. The output of the logic circuit 105 is modulated by the modulation circuit 103 and then radiated as radio waves from the antenna circuit 402. The modulation circuit 103 performs modulation by mixing the output of the oscillation circuit 102 and the output of the logic circuit 105.

As the sensor circuit 107, for example, a pressure sensor, a photosensor, an odor sensor, a sound sensor, and the like can be used, but the invention is not limited to these. The memory circuit 108 is used for storing information that has been sensed, and is preferably nonvolatile memory, but the invention is not limited to this. Even when the memory circuit 108 is volatile memory, it can function in the same way as nonvolatile memory as long it can secure a power supply. The memory circuit 108 can be, for example, SRAM, DRAM, flash memory, EEPROM, FeRAM, or the like.

Embodiment Mode 3

Figure 5:
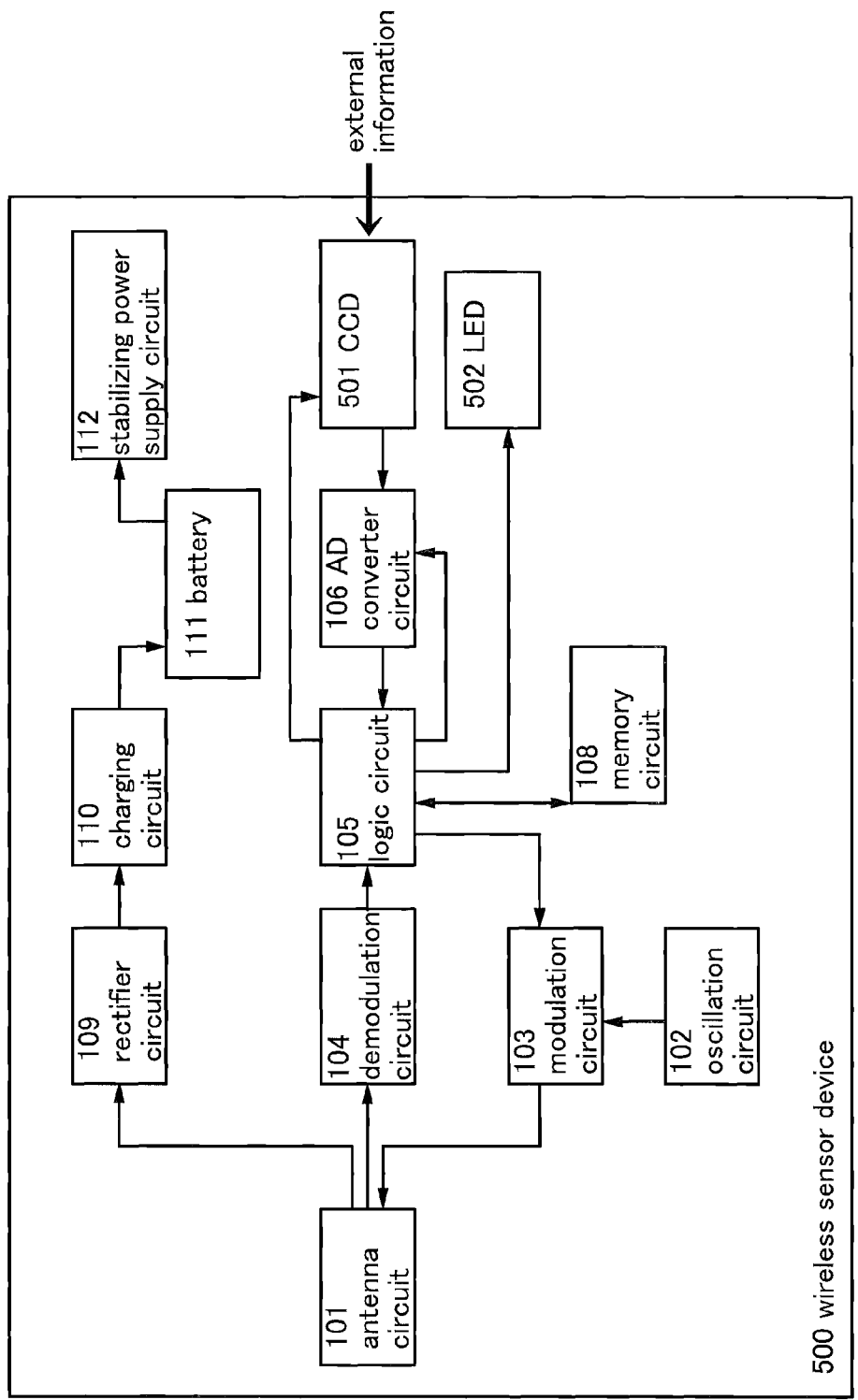
FIG. 5 is a block diagram illustrating the configuration of a wireless sensor device of the invention.

Embodiment Mode 3 of the invention is shown in FIG. 5. FIG. 5 illustrates a block diagram of the invention. A wireless sensor device 500 includes the antenna circuit 101, the oscillation circuit 102, the modulation circuit 103, the demodulation circuit 104, the logic circuit 105, the AD converter circuit 106, the memory circuit 108, the rectifier circuit 109, the charging circuit 110, the battery 111, the stabilizing power supply circuit 112, a CCD 501, and an LED 502.

In this embodiment mode, the wireless sensor device 500 includes the LED 502 and the CCD 501, so that light emitted from the LED 502 illuminates inside of the body and the CCD 501 shoots an image of the illuminated object. A light-emission source is not limited to the LED and other types of light emitter such as an EL element can also be used. In addition, the image pickup device is not limited to the CCD, and a CMOS sensor or the like can also be used, for example.

In the case of performing communication with a magnetic field, the antenna circuit 101 includes, as shown in FIG. 3A, the coiled antenna 301 and the tuning capacitor 302. The rectifier circuit 109 includes, as shown in FIG. 3B, the diode 303, the diode 304, and the smoothing capacitor 305. However, the configurations of the antenna circuit 101 and the rectifier circuit 109 are not limited to them. In the case of performing communication with not a magnetic field but an electric field, the antenna does not need to be in a coiled form.

The operation of the wireless sensor device 500 in this embodiment mode will now be described. An AC signal received at the antenna circuit 101 is half-wave rectified by the diodes 303 and 304, and then smoothed by the smoothing capacitor 305. By this smoothed voltage, the charging circuit 110 is activated to charge the battery 111. As the battery 111, for example, a secondary battery, a high-capacity capacitor, or the like can be used.

An output voltage of the battery 111 is stabilized by the stabilizing power supply circuit 112, and the stabilized voltage is supplied to the oscillation circuit 102, the modulation circuit 103, the demodulation circuit 104, the logic circuit 105, the AD converter circuit 106, the memory circuit 108, the CCD 501, and the LED 502.

Signals communicated with an external device are transmitted through carrier modulation. Therefore, the wireless sensor device of the invention should demodulate the modulated signal. Examples of the carrier frequency include, but not limited to, 125 kHz, 13.56 MHz, 950 MHz, and the like. In addition, examples of a modulation method include, but not limited to, amplitude modulation, frequency modulation, phase modulation, and the like.

A signal input to the antenna circuit 101 is demodulated in the demodulation circuit 104. The demodulated signal is processed in the logic circuit 105. When the input signal is an encoded signal, it is decoded in the logic circuit 105. For example, when the signal from the external transmitter has been encoded with modified Miller codes, NRZ-L codes, or the like, the encoded signal is decoded in the logic circuit 105. The decoded data is transmitted to the AD converter circuit 106 and the CCD 501, whereby the AD converter circuit 106 and the CCD 501 are activated.

With the activated CCD 501, the wireless sensor device 500 can shoot an external image. While the CCD 501 is shooting an image, the LED 502 is lighting. The output of the CCD 501 is converted into a digital signal by the AD converter circuit 106. The output signal of the AD converter circuit 106 is processed by the logic circuit 105. For example, the signal is encoded by the logic circuit 105 when necessary. The output of the logic circuit 105 is modulated by the modulation circuit 103 and output from the antenna circuit 101. The modulation circuit 103 performs modulation by mixing the output of the oscillation circuit 102 and the output of the logic circuit 105. The memory circuit 108 is used for storing information that has been sensed, and is preferably nonvolatile memory, but the invention is not limited to this. Even when the memory circuit 108 is volatile memory, it can function in the same way as nonvolatile memory as long it can secure a power supply. The memory circuit 108 can be, for example, SRAM, DRAM, flash memory, EEPROM, FeRAM, or the like.

As described above, using the image pickup device such as a CCD, the wireless sensor device of this embodiment mode can shoot an internal image of the body. Thus, abnormality of inside of the body can be detected at an early stage, which greatly contributes to maintaining one's health.

Embodiment 1

Figure 6:
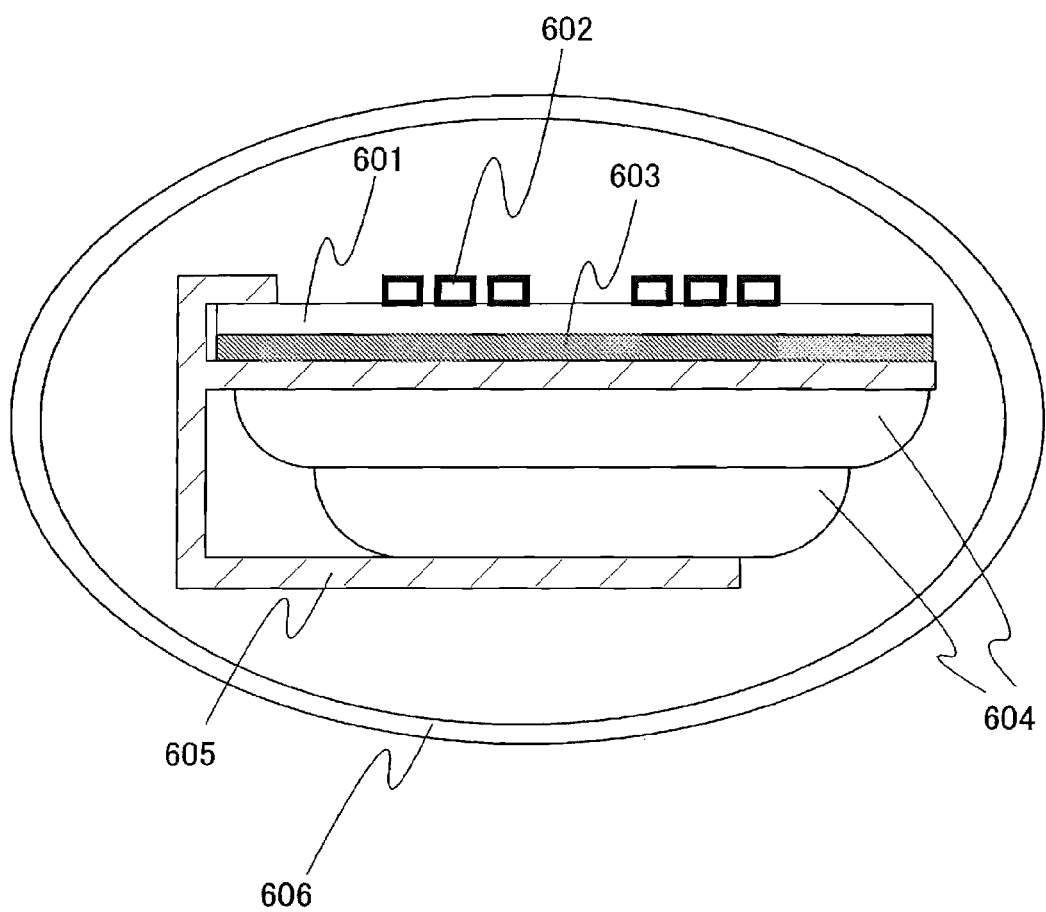
FIG. 6 is a cross-sectional view of a wireless sensor device of the invention.

Embodiment 1 of the invention is shown in FIG. 6. FIG. 6 illustrates a cross section of the wireless sensor device of the invention. The wireless sensor device shown in FIG. 6 includes a substrate 601, an antenna 602, a ferrite 603, a secondary battery 604, a flexible printed board 605, and a package 606. The substrate 601 has the above-described rectifier circuit, demodulation circuit, logic circuit, modulation circuit, oscillator circuit, and the like. The substrate is preferably a single-crystalline silicon substrate, a glass substrate, a plastic substrate, or the like, but the invention is not limited to this.

Although the antenna 602 is formed on the substrate 601, the position of the antenna 602 is not limited to this; it is also possible to provide another substrate for forming the antenna 602. In addition, the ferrite 603 is not necessarily required. However, in performing communication with a magnetic flux, using the ferrite 603 can improve the distribution of a magnetic flux and thus can enhance sensitivity. Although a lithium-ion secondary button battery or the like is suitable for the secondary battery 604, the battery is not limited to the lithium-ion battery. Further, the shape of the battery is not limited to the button, and it is also possible to use a high-capacity capacitor such as an electric double layer capacitor. The flexible printed board 605 electrically connects the substrate 601 and the secondary battery 604.

The package 606 should be highly airtight on the assumption that that the package 606 is to be implanted in the body. In addition, the package 606 should be formed from a material having no adverse effects on the living body. In the case of using a secondary button battery, the package can be formed to a thickness of about 1 cm; thus, it can be even swallowed by humans.

Such a highly airtight package cannot be opened frequently. Therefore, when a primary battery which is non-rechargeable is used, the sensor device becomes inactive once the battery has run out. However, when a secondary battery which is wirelessly rechargeable is used as in the invention, the sensor device can be used without concern for the charged level of the battery. Further, even when the sensor device is located inside the body, the battery can be recharged from outside of the body.

Thus, using the wireless sensor device of the invention can acquire physical information by radio communication.

Embodiment 2

Figure 7:
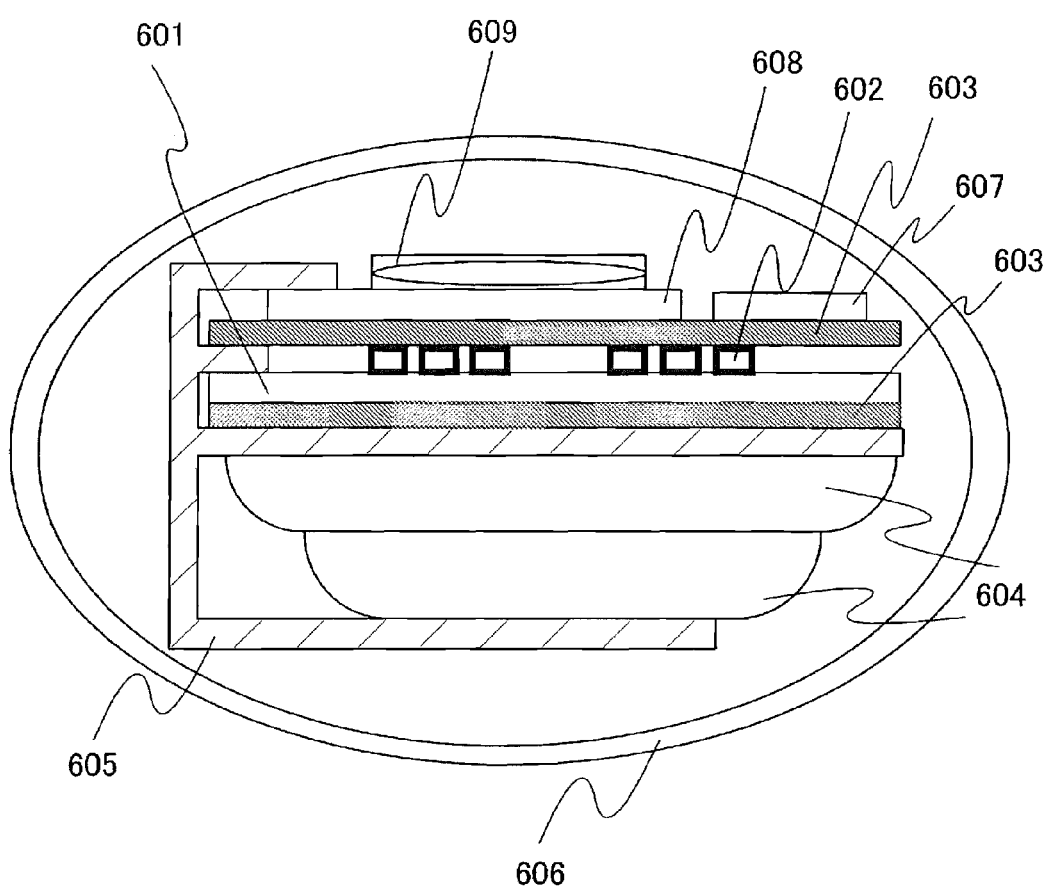
FIG. 7 is a cross-sectional view of a wireless sensor device of the invention.

Embodiment 2 of the invention is shown in FIG. 7. FIG. 7 illustrates a cross section of the wireless sensor device of the invention. The wireless sensor device shown in FIG. 7 includes the substrate 601, the antenna 602, the ferrite 603, the secondary battery 604, the flexible printed board 605, the package 606, an LED 607, a CCD 608, and a lens 609. The substrate 601 has the above-described rectifier circuit, demodulation circuit, logic circuit, modulation circuit, oscillator circuit, and the like. The substrate is preferably a single-crystalline silicon substrate, a glass substrate, a plastic substrate, or the like, but the invention is not limited to this.

Although the antenna 602 is formed on the substrate 601, the position of the antenna 602 is not limited to this; it is also possible to provide another substrate for forming the antenna 602. In addition, the ferrite 603 is not necessarily required. However, in performing communication with a magnetic flux, using the ferrite 603 can improve the distribution of a magnetic flux and thus can enhance sensitivity. Although a lithium-ion secondary button battery is suitable for the secondary battery 604, the battery is not limited to the lithium-ion battery. Further, the shape of the battery is not limited to the button, and it is also possible to use a high-capacity capacitor such as an electric double layer capacitor. The flexible printed board 605 electrically connects the substrate 601 to the secondary battery 604, the CCD 608, and the LED 607.

In the wireless sensor device of this embodiment, the LED 607 is lit to illuminate inside of the body. Then, the CCD 608 shoots an image of the illuminated object through the lens 609. The data shot is transmitted to the substrate 601 through the flexible printed board 605, so that the data is processed and wirelessly transmitted to outside of the body.

The package 606 should be highly airtight on the assumption that the package 606 is to be implanted in the body. In addition, a portion of the package 606 on the periphery of the LED 607 and the lens 609 should be transparent to enable shooting. Further, the package 606 should be formed from a material having no adverse effects on the living body. In the case of using a secondary button battery, the package can be formed to a thickness of about 1 cm; thus, it can be even swallowed by humans.

Such a highly airtight package cannot be opened frequently. Therefore, when a primary battery which is non-rechargeable is used, the sensor device becomes inactive once the battery has run out. However, when a secondary battery which is wirelessly rechargeable is used as in the invention, the sensor device can be used without concern for the charged level of the battery. Further, even when the sensor device is located inside the body, the battery can be recharged from outside of the body. This advantageous effect can be multiplied particularly in the case of mounting a high-power-consumption element such as an LED.

Thus, using the wireless sensor device of the invention can read out physical information by radio communication.

This embodiment can be implemented in combination with any of Embodiment Modes 1 to 3 and Embodiment 1.

Embodiment 3

Figure 8:
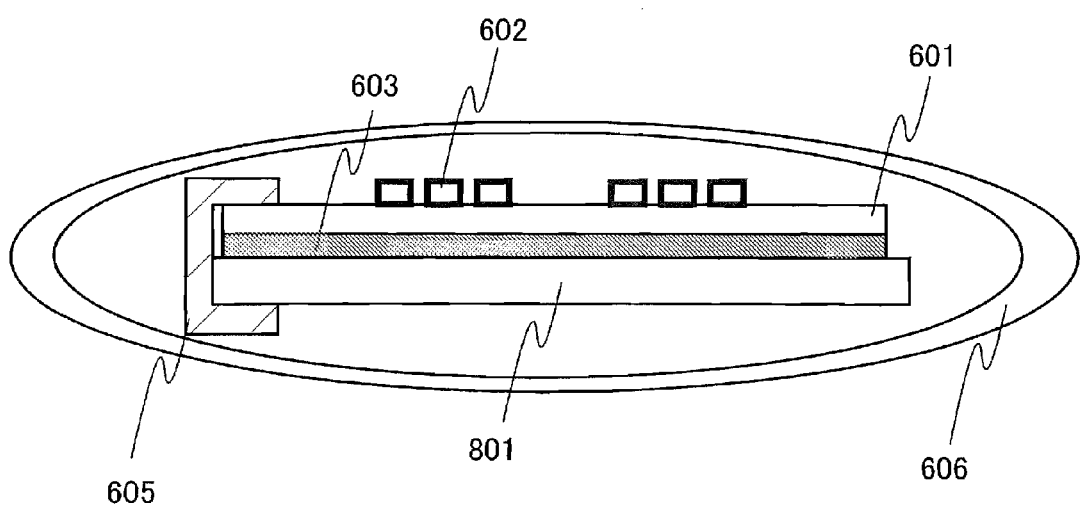
FIG. 8 is a cross-sectional view of a wireless sensor device of the invention.

Embodiment 3 of the invention is shown in FIG. 8. FIG. 8 illustrates a cross section of the wireless sensor device of the invention. The wireless sensor device shown in FIG. 8 includes the substrate 601, the antenna 602, the ferrite 603, a thin-film secondary battery 801, the flexible printed board 605, and the package 606. The substrate 601 has the above-described rectifier circuit, demodulation circuit, logic circuit, modulation circuit, oscillator circuit, and the like. The substrate is preferably a single-crystalline silicon substrate, a glass substrate, a plastic substrate, or the like, but the invention is not limited to this.

Although the antenna 602 is formed on the substrate 601, the position of the antenna 602 is not limited to this; it is also possible to provide another substrate for forming the antenna 602. In addition, the ferrite 603 is not necessarily required. However, in performing communication with a magnetic flux, using the ferrite 603 can improve the distribution of a magnetic flux and thus can enhance sensitivity. A thin-film lithium-ion secondary battery is used for the thin-film secondary battery 801. When such a thin-film lithium-ion battery is used, the thickness of the secondary battery can be made 1 mm or less. The flexible printed board 605 electrically connects the substrate 601 and the thin-film secondary battery 801. The wireless sensor device of this embodiment can be formed to have a total thickness of 2 mm or less, whereby it can be implanted even under the skin of a human body.

The package 606 should be highly airtight on the assumption that the package 606 is to be implanted in the body. However, such a highly airtight package cannot be opened frequently. Therefore, when a primary battery which is non-rechargeable is used, the sensor device becomes inactive once the battery has run out. However, when a secondary battery which is wirelessly rechargeable is used as in the invention, the sensor device can be used without concern for the charged level of the battery. Further, even when the sensor device is located inside the body, the battery can be recharged from outside of the body.

Thus, using the wireless sensor device of the invention can acquire physical information by radio communication.

This embodiment can be implemented in combination with any of Embodiment Modes 1 to 3 and Embodiments 1 and 2.

Embodiment 4

Figure 9:
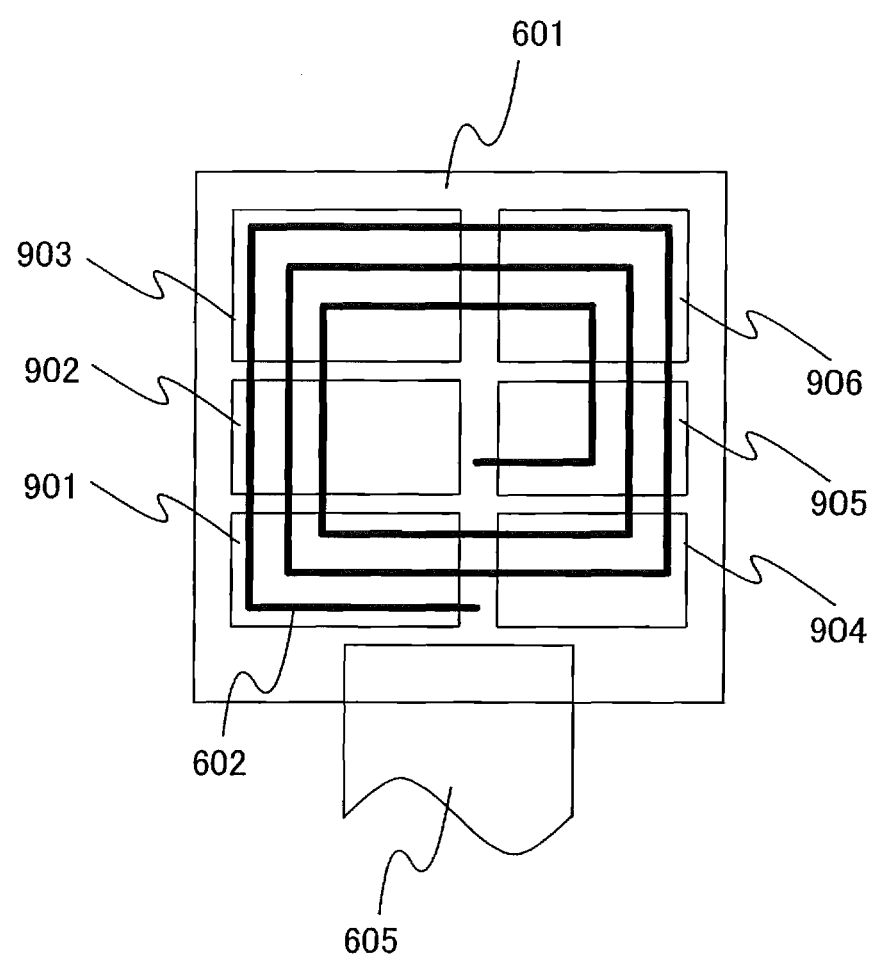
FIG. 9 is a top view of a substrate of a wireless sensor device of the invention.

Embodiment 4 of the invention is shown in FIG. 9. FIG. 9 is a top view of a substrate provided with circuits. For the substrate 601, a single-crystalline silicon substrate, a glass substrate, a plastic substrate, or the like can be used, but the invention is not limited to this.

Circuits 901 to 906 represent circuits formed over the substrate 601. The circuits 901 to 906 include, for example, the oscillation circuit, the modulation circuit, the demodulation circuit, the logic circuit, the AD converter circuit, the sensor circuit, the memory circuit, the rectifier circuit, the charging circuit or the stabilizing power supply circuit, and the like that are shown in FIG. 1. The antenna 602 is formed over the circuits 901 to 906. The flexible printed board 605 for connection with a battery such as a secondary battery or an electric double layer capacitor is electrically connected to the circuits 901 to 906 over the substrate 601.

This embodiment can be implemented in combination with any of Embodiment Modes 1 to 3 and Embodiments 1 to 3.

Embodiment 5

Figure 12:
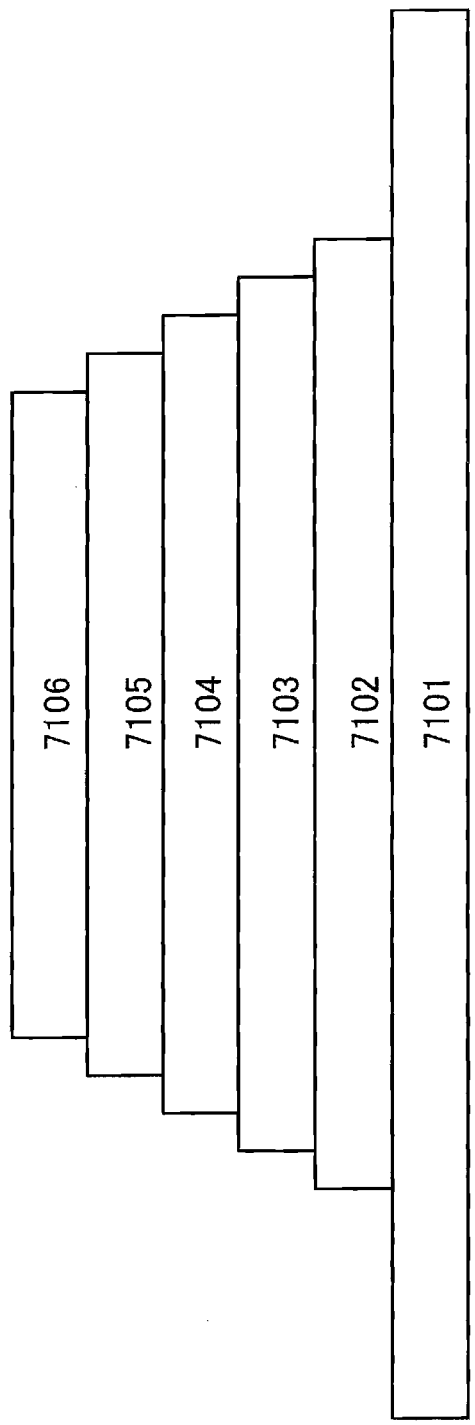
FIG. 12 is a cross-sectional view of a thin-film secondary battery.

Embodiment 5 of the invention is shown in FIG. 12. FIG. 12 illustrates a cross-sectional view of a thin-film secondary battery. Hereinafter, description will be given of the thin-film secondary battery used in Embodiment 3. Secondary batteries include nickel-cadmium batteries, lithium-ion batteries, lead batteries, and the like. Among them, lithium-ion batteries, which have no memory effects and can discharge a large amount of current, have been widely used.

In recent years, research has been conducted on fabrication of thinner lithium-ion batteries. Among them, there has emerged a lithium-ion battery having a thickness of one to several μm. Such a thin-film secondary battery can be used as a flexible secondary battery.

First, a current-collecting thin film 7102 to serve as an electrode is formed over a substrate 7101. The current-collecting thin film 7102 should have high adhesion to an upper negative electrode active material layer 7103 and have low resistance. Specifically, aluminum, copper, nickel, vanadium, or the like can be used for the current-collecting thin film 7102.

Next, the negative electrode active material layer 7103 is formed over the current-collecting thin film 7102. Generally, vanadium oxide or the like is used for the negative electrode active material layer 7103. Next, a solid electrolyte layer 7104 is formed over the negative electrode active material layer 7103. Generally, lithium phosphate or the like is used for the solid electrolyte layer 7104. Next, a positive electrode active material layer 7105 is formed over the solid electrolyte layer 7104. Generally, lithium manganate or the like is used for the positive electrode active material layer 7105. Lithium cobaltate or lithium nickel oxide may also be used. Next, a current-collecting thin film 7106 to serve as an electrode is formed over the positive electrode active material layer 7105. The current-collecting thin film 7106 should have high adhesion to the positive electrode active material layer 7105 and have low resistance. For example, aluminum, copper, nickel, vanadium, or the like can be used. Each layer may be formed by using either a sputtering technique or an evaporation technique. In addition, the thickness of each layer is preferably 0.1 to 3 μm.

Next, charging and discharging operations will be described. In charging the battery, lithium ions are desorbed from the positive electrode active material layer 7105. Then, the lithium ions are absorbed into the negative electrode active material layer 7103 through the solid electrolyte layer 7104. At this time, electrons are released to outside from the positive electrode active material layer 7105. In discharging the battery, on the other hand, lithium ions are desorbed from the negative electrode active material layer 7103. Then, the lithium ions are absorbed into the positive electrode active material layer 7105 through the solid electrolyte layer 7104. At this time, electrons are released to outside from the negative electrode active material layer 7103. The thin-film secondary battery operates in this manner. With such a thin-film secondary battery, a compact and lightweight battery can be constructed.

This embodiment can be implemented in combination with any of Embodiment Modes 1 to 3 and Embodiments 1 to 4.

Embodiment 6

Figure 10A:
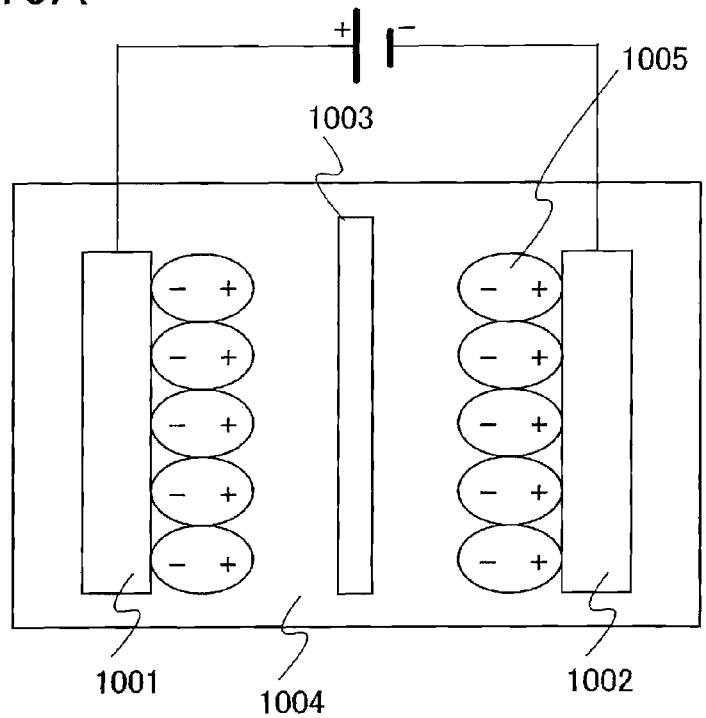
FIGS. 10A and 10B illustrate an electric double layer capacitor.

Embodiment 6 of the invention is shown in FIGS. 10A to 11B. This embodiment will describe an electric double layer capacitor. The structure of the electric double layer capacitor is shown in FIG. 10A.

Figure 10B:
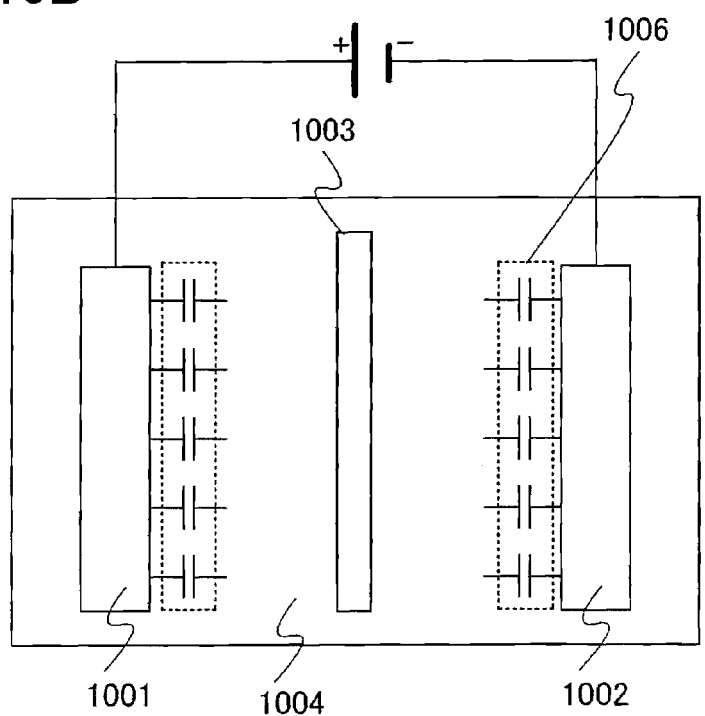

Two electrodes (a positive electrode 1001 and a negative electrode 1002) are put in an electrolyte 1004, and a voltage is applied across the two electrodes. A separator 1003 is disposed between the positive electrode 1001 and the negative electrode 1002 so that these electrodes are not shorted in the electrolyte. Generally, the electrolyte 1004 starts to be electrolyzed at a voltage of about 1 V so that a current flows between the electrodes, although the voltage level differs depending on the kind of the electrolyte 1004. However, when the voltage across the two electrodes is low, electrolysis reaction does not occur. At this time, a layer of polarized ions 1005 is formed around the electrodes as shown in FIG. 10A. Such layer of the polarized ions 1005 is referred to as an electric double layer, and can be used as a capacitor 1006 as shown in FIG. 10B. A capacitor using an electric double layer has the following features.

The layer of the polarized ions is very thin. Therefore, when an electrode with a large surface area is prepared, a capacitor with a high capacitance value can be formed. The thinnest electric double layer is as thin as one molecule.

Figure 11A:
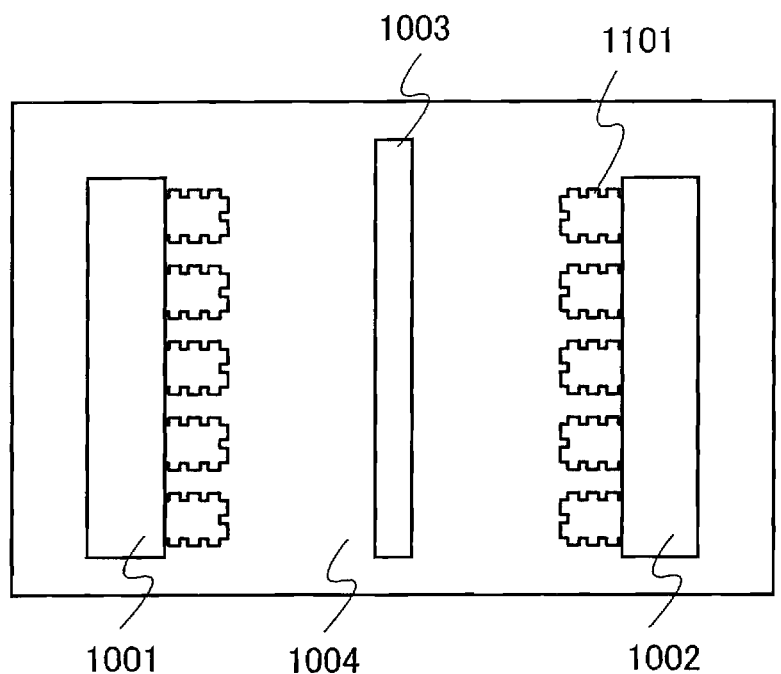
FIGS. 11A and 11B illustrate an electric double layer capacitor.
Figure 11B:
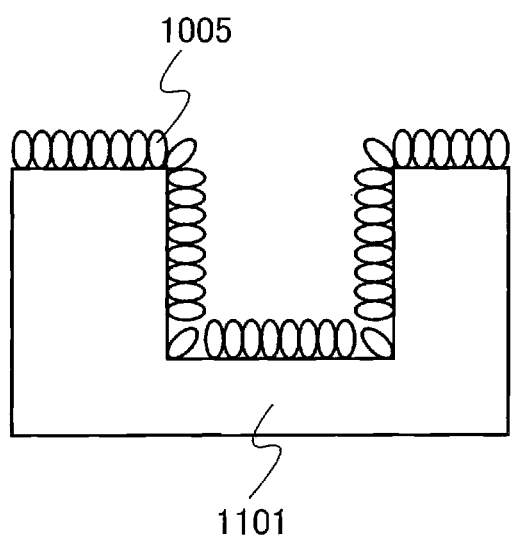

In order to prepare an electrode with a large surface area, activated carbon 1101 is attached to the surfaces of the positive electrode 1001 and the negative electrode 1002 as shown in FIG. 11A, so that the surface of the activated carbon is also used as the electrode. Having a large surface area, the activated carbon 1101 is effective for forming an electric double layer with a large area. A magnified view of the activated carbon 1101 is shown in FIG. 11B. The polarized ions 1005 are formed on the surface of the activated carbon 1101, thereby functioning as the capacitor 1006. Such a capacitor 1006 can function as a capacitor only at a voltage lower than the voltage level at which electrolysis reaction occurs, and has a disadvantage in low withstand voltage. However, when such an electric double layer capacitor is used, it is possible to obtain a capacitor with a small volume and a high capacitance value. Specifically, a capacitor of 0.1 F or more, which has a size of about a coin, can be obtained.

This embodiment can be implemented in combination with any of Embodiment Modes 1 to 3 and Embodiments 1 to 5.

Embodiment 7

Figure 13A:
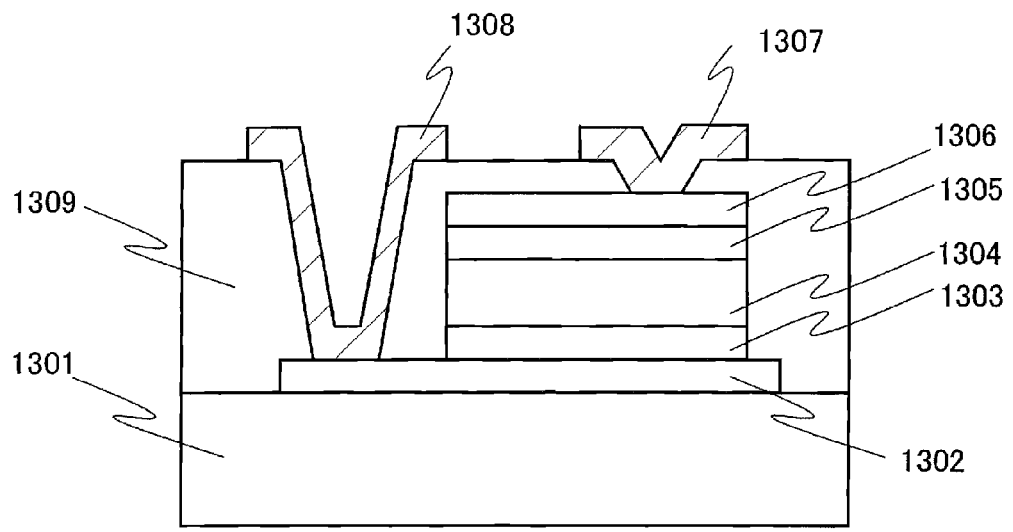
FIGS. 13A and 13B illustrate an embodiment of a photosensor.
Figure 13B:
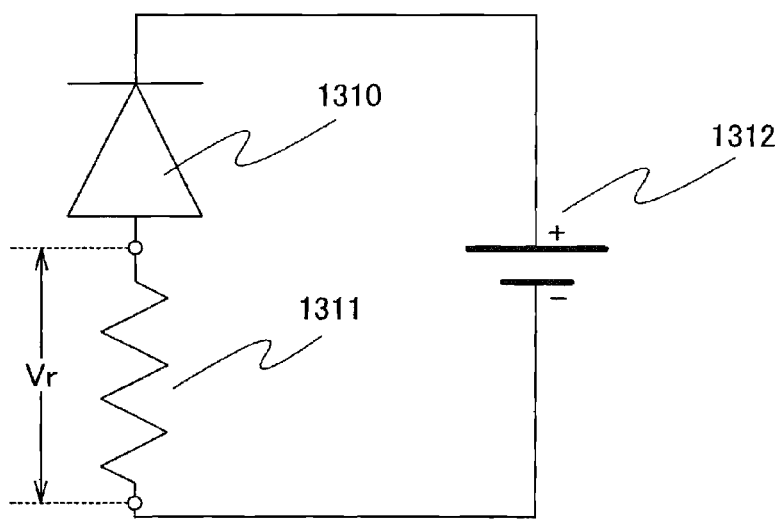

Embodiment 7 of the invention is shown in FIGS. 13A and 13B. FIGS. 13A and 13B illustrate specific examples of a photosensor.

FIG. 13A is a cross-sectional view of a photosensor. The photosensor of this embodiment uses a PIN diode. First, a transparent conductive film 1302 is formed over a substrate 1301. Then, p-type amorphous silicon 1303, i-type amorphous silicon 1304, n-type amorphous silicon 1305, and an electrode 1306 are sequentially formed and patterned into predetermined shapes. Then, an interlayer film 1309 is formed and contact holes are formed in the interlayer film 1309 so as to partially expose the transparent conductive film 1302 and the electrode 1306. Then, an electrode 1308 connected to the transparent conductive film 1302 at the contact hole as well as an electrode 1307 connected to the electrode 1306 at the contact hole are formed.

FIG. 13B shows a connection relation between the photosensor and other elements in a sensor circuit. A resistor 1311 is connected to a PIN diode 1310 and a reverse-bias voltage is applied to the PIN diode 1310 by a power supply 1312. When the PIN diode 1310 receives light, a photocurrent flows through the PIN diode 1310, and a voltage Vr is generated across opposite terminals of the resistor 1311. By reading out this voltage Vr, the amount of light can be detected.

This embodiment can be implemented in combination with any of Embodiment Modes 1 to 3 and Embodiments 1 to 6.

Embodiment 8

Figure 14:
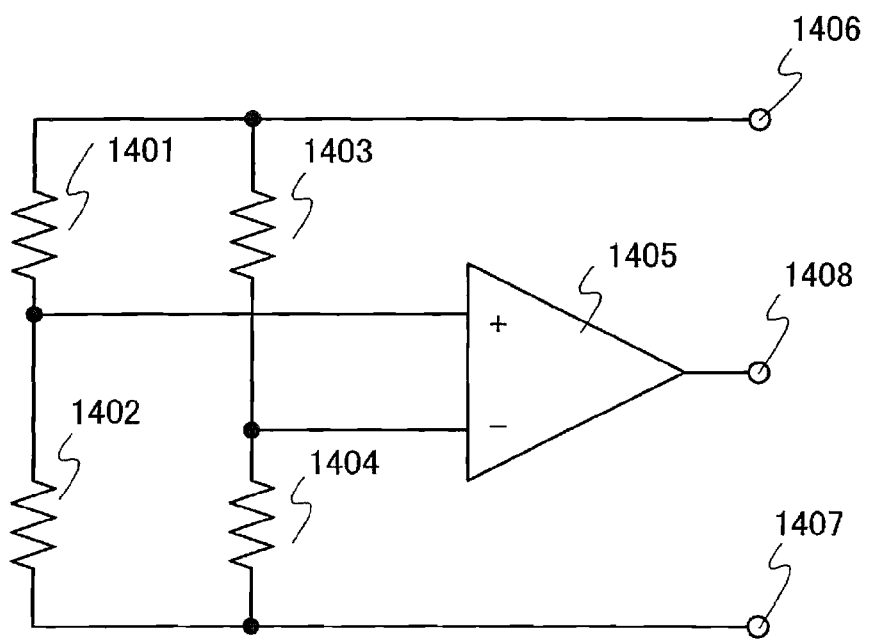
FIG. 14 illustrates an embodiment of a pressure sensor.

Embodiment 8 of the invention is shown in FIG. 14. FIG. 14 illustrates an example of a pressure sensor. The pressure sensor of this embodiment includes resistors formed from semiconductors (semiconductor resistors) 1401 to 1404, a differential amplifier 1405, power supply terminals 1406 and 1407, and an output terminal 1408.

The resistors 1401 and 1402 are connected in series between the power supply terminals 1406 and 1407. Similarly, the resistors 1403 and 1404 are connected in series between the power supply terminals 1406 and 1407. The resistors 1401 and 1402 are connected in parallel with the resistors 1403 and 1404. The resistors 1401 and 1402 are connected to the differential amplifier 1405 such that a potential between the resistors 1401 and 1402 is input to a non-inverting input terminal (+) of the differential amplifier 1405. Similarly, the resistors 1403 and 1404 are connected to the differential amplifier 1405 such that a potential between the resistors 1403 and 1404 is input to an inverting input terminal (−) of the differential amplifier 1405.

The resistance value of a normal semiconductor resistor changes in response to pressure applied, due to a piezoelectric effect. When pressure is applied to the pressure sensor of this embodiment, pressures with different levels are applied to the resistors 1401 and 1404. Upon application of pressure, potentials input to the inverting input terminal (−) and the non-inverting input terminal (+) of the differential amplifier change. By amplifying the potential difference, the presence of pressure can be detected. When this pressure sensor is used for the above-described wireless sensor device, information acquired by the sensor circuit can be transmitted as radio waves.

Note that a pressure sensor used in the invention is not limited to the configuration shown in this embodiment, and a circuit with a different structure may be used.

As described above, the applicable range of the invention is so wide that it can be applied to any wireless sensor device which transmits information that is sensed. In addition, this embodiment can be implemented in combination with any of Embodiment Modes 1 to 3 and Embodiments 1 to 7.

Embodiment 9

Next, a method of fabricating the wireless sensor device of the invention will be described in detail. Although this embodiment illustrates a thin film transistor (TFT) as an exemplary semiconductor element, a semiconductor element used in the wireless sensor device of the invention is not limited to this. For example, not only a TFT but also a memory element, a diode, a resistor, a coil, a capacitor, an inductor, or the like can be used.

This embodiment will describe an example where the thin-film secondary battery shown in Embodiment 5 is used as a battery, and an antenna, the battery, and a semiconductor element are all formed over the same substrate. When the antenna, the battery, and the semiconductor element are all formed over the same substrate, a compact wireless sensor device can be provided. Note that the invention is not limited to this structure, and it is also possible to separately form an antenna or a battery and a semiconductor element, and electrically connect them afterwards.

First, as shown in FIG. 15A, an insulating film 701, a release layer 702, an insulating film 703 functioning as a base film, and a semiconductor film 704 are sequentially formed over a heat-resistant substrate 700. The insulating film 701, the release layer 702, the insulating film 703, and the semiconductor film 704 can be formed in succession.

For the substrate 700, it is possible to use, for example, a glass substrate made of barium borosilicate glass, aluminoborosilicate glass, or the like; a quartz substrate; a ceramic substrate; or the like. It is also possible to use a metal substrate such as a stainless steel substrate or a semiconductor substrate such as a silicon substrate. A substrate made of a flexible synthetic resin, e.g., plastic generally has a lower allowable temperature limit than the above-described substrates; however, such substrate can be used as long as it can withstand the processing temperature in the fabrication process.

Examples of a plastic substrate include polyester typified by polyethylene terephthalate (PET), polyethersulfone (PES), polyethylene naphthalate (PEN), polycarbonate (PC), nylon, polyetheretherketone (PEEK), polysulfone (PSF), polyetherimide (PEI), polyarylate (PAR), polybutylene terephthalate (PBT), polyimide, acrylonitrile-butadiene-styrene resin, polyvinyl chloride, polypropylene, polyvinyl acetate, acrylic resin, and the like.

Although the release layer 702 is provided over the entire surface of the substrate 700 in this embodiment, the invention is not limited to this structure. For example, the release layer 702 may be formed partially over the substrate 700 by a photolithography method or the like.

The insulating films 701 and 703 are formed by depositing an insulating material such as silicon oxide, silicon nitride (e.g., $SiN_x$ or $Si_3N_4$), silicon oxynitride ($SiO_xN_y$, where $x>y>0$), or silicon nitride oxide ($SiN_xO_y$, where $x>y>0$) by a CVD method, a sputtering method, or the like.

The insulating films 701 and 703 are provided to prevent an alkali metal such as Na or an alkaline earth metal contained in the substrate 700 from being diffused into the semiconductor film 704, which would otherwise adversely affect the characteristics of semiconductor elements such as TFTs. In addition, the insulating film 703 functions to prevent an impurity element contained in the release layer 702 from being diffused into the semiconductor film 704, and also functions to protect the semiconductor elements in the later step of peeling the semiconductor elements.

Each of the insulating films 701 and 703 can be either a single insulating film or stacked layers of a plurality of insulating films. In this embodiment, the insulating film 703 is formed by sequentially depositing a silicon oxynitride film to a thickness of 100 nm, a silicon nitride oxide film to a thickness of 50 nm, and a silicon oxynitride film to a thickness of 100 nm. However, the material and thickness of each film as well as the number of stacked layers are not limited to this example. For example, the bottom silicon oxynitride film may be replaced with a siloxane resin having a thickness of 0.5 to 3 μm that is formed by a spin coating method, a slit coating method, a droplet discharge method, a printing method, or the like. In addition, the middle silicon nitride oxide film may be replaced with a silicon nitride (e.g., $SiN_x$ or $Si_3N_4$) film. Further, the top silicon oxynitride film may be replaced with a silicon oxide film. The thickness of each film is preferably 0.05 to 3 μm, and can be freely selected within this range.

Alternatively, it is also possible to form the bottom layer of the insulating film 703, which is closest to the release layer 702, using a silicon oxynitride film or a silicon oxide film, form the middle layer using a siloxane resin, and form the top layer using a silicon oxide film.

Note that a siloxane resin is a resin formed from a siloxane material as a starting material and having the bond of Si—O—Si. A siloxane resin may contain as a substituent at least one of fluorine, an alkyl group, and aromatic hydrocarbon, in addition to hydrogen.

The silicon oxide film can be formed by thermal CVD, plasma CVD, atmospheric pressure CVD, bias ECRCVD, or the like, using a mixed gas of $SiH_4/O_2$, TEOS(tetraethoxysilane)/$O_2$, or the like. The silicon nitride film can be typically formed by plasma CVD using a mixed gas of $SiH_4/NH_3$. The silicon oxynitride film and the silicon nitride oxide film can be typically formed by plasma CVD using a mixed gas of $SiH_4/N_2O$.

For the release layer 702, it is possible to use a metal film, a metal oxide film, or a stacked film of a metal film and a metal oxide film. The metal film and the metal oxide film can be either a single layer or a stacked structure of a plurality of layers. In addition to a metal film or a metal oxide film, metal nitride or metal oxynitride can also be used. The release layer 702 can be formed by a sputtering method or various CVD methods such as a plasma CVD method.

Examples of metals used for the release layer 702 include tungsten (W), molybdenum (Mo), titanium (Ti), tantalum (Ta), niobium (Nb), nickel (Ni), cobalt (Co), zirconium (Zr), zinc (Zn), ruthenium (Ru), rhodium (Rh), palladium (Pd), osmium (Os), iridium, and the like. In addition to such metal films, the release layer 702 can also be formed using a film made of an alloy containing the above-described metal as a main component or a compound containing the above-described metal.

Alternatively, the release layer 702 can also be formed using a single silicon (Si) film or a film made of a compound containing silicon (Si) as a main component. As a further alternative, the release layer 702 can also be formed using a film made of an alloy of silicon (Si) and the above-described metal. A film containing silicon can have any of amorphous, microcrystalline, and polycrystalline structures.

The release layer 702 can be either a single layer of the above-described film or stacked layers thereof. The release layer 702 having a stack of a metal film and a metal oxide film can be formed by sequentially forming a base metal film and oxidizing or nitriding the surface of the metal film. Specifically, plasma treatment may be applied to the base metal film in an oxygen atmosphere or an $N_2O$ atmosphere, or thermal treatment may be applied to the metal film in an oxygen atmosphere or an $N_2O$ atmosphere. Alternatively, oxidation can be accomplished by forming a silicon oxide film or a silicon oxynitride film on the base metal film. Similarly, nitridation can be accomplished by forming a silicon oxynitride film or a silicon nitride film on the base metal film.

As the plasma treatment for oxidation or nitridation of the metal film, it is possible to perform high-density plasma treatment with a plasma density of $1\times10^{11}$ cm$^{-3}$ or higher, preferably in the range of $1\times10^{11}$ to $9\times10^{15}$ cm$^{-3}$ and with high frequency such as microwaves (e.g., a frequency of 2.45 GHz).

Although the release layer 702 having a stack of a metal film and a metal oxide film can be formed by oxidizing the surface of the base metal film, it is also possible to sequentially form a metal film and form a metal oxide film thereon.

For example, in the case of using tungsten as a metal, a tungsten film is formed as a base metal film by a sputtering method, a CVD method, or the like, and then plasma treatment is applied to the tungsten film Accordingly, a tungsten film that is a metal film and a metal oxide film that is in contact with the metal film and is formed from oxide of tungsten can be formed.

Note that oxide of tungsten is given by $WO_x$ where x is in the range of 2 to 3. There are cases where x is 2 ($WO_2$), x is 2.5 ($W_2O_5$), x is 2.75 ($W_4O_{11}$), and x is 3 ($WO_3$). In formation of oxide of tungsten, there is no limitation on the value of x, and the value of x may be determined based on the etching rate or the like.

It is preferable that the semiconductor film 704 be consecutively formed after the formation of the insulating film 703 without exposure to air. The thickness of the semiconductor film 704 is 20 to 200 nm (preferably 40 to 170 nm, or more preferably 50 to 150 nm). Note that the semiconductor film 704 may be either an amorphous semiconductor or a polycrystalline semiconductor. Further, not only silicon but also silicon germanium can be used for the semiconductor. In the case of using silicon germanium, the concentration of germanium is preferably about 0.01 to 4.5 atomic %.

Note that the semiconductor film 704 can be crystallized by a known technique. As a known crystallization method, there are a laser crystallization method with laser light and a crystallization method with a catalytic element. Alternatively, it is also possible to combine a crystallization method with a catalytic element and a laser crystallization method. In the case of using a thermally stable substrate such as quartz for the substrate 700, it is possible to combine any of the following crystallization methods: a thermal crystallization method with an electrically heated oven, a lamp anneal crystallization method with infrared light, a crystallization method with a catalytic element, and high temperature annealing at about 950° C.

For example, in the case of using laser crystallization, thermal treatment at 550° C. is applied to the semiconductor film 704 for four hours before the laser crystallization, in order to enhance the resistance of the semiconductor film 704 to laser. When a continuous-wave solid-state laser is used and irradiation is conducted with the second to fourth harmonics of the fundamental wave, crystals with a large grain size can be obtained. Typically, the second harmonic (532 nm) or the third harmonic (355 nm) of an Nd:$YVO_4$ laser (the fundamental wave of 1064 nm) is preferably used. Specifically, laser light emitted from a continuous-wave $YVO_4$ is converted into a harmonic with a nonlinear optical element, so that laser light having an output of 10 W is obtained. Then, the laser light is preferably shaped into a rectangular shape or an elliptical shape with optics on the irradiation surface. In this case, a laser power density of about 0.01 to 100 MW/cm$^2$ (preferably, 0.1 to 10 MW/cm$^2$) is required, and irradiation is conducted with a scanning rate of about 10 to 2000 cm/sec.

As a continuous-wave gas laser, an Ar laser, a Kr laser, or the like can be used. As a continuous-wave solid-state laser, the following can be used: a YAG laser, a $YVO_4$ laser, a YLF laser, a $YAlO_3$ laser, a forsterite ($Mg_2SiO_4$) laser, a $GdVO_4$ laser, a $Y_2O_3$ laser, a glass laser, a ruby laser, an alexandrite laser, a Ti:sapphire laser, and the like.

Alternatively, the following pulsed lasers can be used: an Ar laser, a Kr laser, an excimer laser, a $CO_2$ laser, a YAG laser, a $Y_2O_3$ laser, a $YVO_4$ laser, a YLF laser, a $YAlO_3$ laser, a glass laser, a ruby laser, an alexandrite laser, a Ti:sapphire laser, a copper vapor laser, and a gold vapor laser.

The repetition rate of pulsed laser light may be set at 10 MHz or higher, so that laser crystallization can be performed with a considerably higher repetition rate than the normally used repetition rates in the range of several ten to several hundred Hz. It is said that it takes several ten to several hundred nseo for the semiconductor film 704 to become completely solidified after being irradiated with pulsed laser light. Therefore, by using laser light with the above-described repetition rate, the semiconductor film 704 can be irradiated with the next laser pulse after it is melted by the previous laser light but before it becomes solidified. Accordingly, the solid-liquid interface of the semiconductor film 704 can be moved continuously and, thus, the semiconductor film 704 having crystal grains that have grown in the scanning direction can be formed. Specifically, it is possible to form an aggregation of crystal grains having a width of about 10 to 30 μm in the scanning direction and a width of about 1 to 5 μm in a direction perpendicular to the scanning direction. By forming single crystals with crystal grains that have continuously grown in the scanning direction, it is possible to form the semiconductor film 704 having few crystal grains at least in the channel direction of a TFT.

Note that laser crystallization can be performed by irradiation with a fundamental wave of continuous-wave laser light and a harmonic of continuous-wave laser light in parallel.

Alternatively, laser crystallization can also be performed by irradiation with a fundamental wave of continuous-wave laser light and a harmonic of pulsed laser light in parallel.

Note that laser irradiation can be performed in an inert gas atmosphere such as a rare gas or a nitrogen gas. Accordingly, roughness of the semiconductor surface by laser irradiation can be suppressed, and variations in threshold voltage of TFTs resulting from variations in interface state density can be suppressed.

By the above-described laser irradiation, the semiconductor film 704 with enhanced crystallinity can be formed. Note that it is also possible to use a polycrystalline semiconductor, which is formed by a sputtering method, a plasma CVD method, a thermal CVD method, or the like, for the semiconductor film 704.

Although the semiconductor film 704 is crystallized in this embodiment, it is not necessarily required to be crystallized and can remain as an amorphous silicon film or a microcrystalline semiconductor film to proceed to the following process. A TFT formed using an amorphous semiconductor or a microcrystalline semiconductor involves less fabrication steps than TFTs formed using a polycrystalline semiconductor. Therefore, it has an advantage of low cot and high yield.

Further, it is also possible to use a single-crystalline semiconductor film formed on an insulating film (SOI: Silicon on Insulator), which is formed by a bonding method or a SIMOX (Separation by IMplanted OXygen) method, for an active layer of a TFT.

An amorphous semiconductor can be obtained by decomposing a gas containing silicon by glow discharge. Examples of a gas containing silicon include $SiH_4$, $Si_2H_6$, and the like. The gas containing silicon may be diluted with hydrogen or with hydrogen and helium.

Next, as shown in FIG. 15B, the semiconductor film 704 is patterned into predetermined shapes, so that island-shaped semiconductor films 705 to 709 are formed. Then, a gate insulating film 710 is formed so as to cover the island-shaped semiconductor films 705 to 709. The gate insulating film 710 can be formed by depositing a film containing silicon nitride, silicon oxide, silicon nitride oxide, or silicon oxynitride, either in a single layer or stacked layers by a plasma CVD method, a sputtering method, or the like. When the gate insulating film 710 is formed to have stacked layers, it is preferable to form a three-layer structure in which a silicon oxide film, a silicon nitride film, and a silicon oxide film are sequentially stacked over the substrate 700.

The gate insulating film 710 can also be formed by oxidizing or nitriding the surfaces of the island-shaped semiconductor films 705 to 709 by high-density plasma treatment. High-density plasma treatment is performed by using, for example, a mixed gas of a rare gas such as He, Ar, Kr, or Xe; and oxygen, nitrogen oxide, ammonia, nitrogen, or hydrogen. When plasma is excited by introduction of microwaves, plasma with a low electron temperature and high density can be generated. When the surfaces of the semiconductor films are oxidized or nitrided by oxygen radicals (there may also be OH radicals) or nitrogen radicals (there may also be NH radicals) generated by such high-density plasma, an insulating film with a thickness of 1 to 20 nm, typically 5 to 10 nm is formed to be in contact with the semiconductor films. Such an insulating film having a thickness of 5 to 10 nm is used as the gate insulating film 710.

Oxidation or nitridation of the semiconductor films by the above-described high-density plasma treatment proceeds by solid-phase reaction. Therefore, interface state density between the gate insulating film and the semiconductor films can be suppressed quite low. Further, by directly oxidizing or nitriding the semiconductor films by high-density plasma treatment, variations in thickness of the insulating film to be formed can be suppressed. Furthermore, in the case where the semiconductor films have crystallinity and the surfaces of the semiconductor films are oxidized by solid-phase reaction by high-density plasma treatment, crystal grain boundaries can be prevented from being locally oxidized at a fast speed. Thus, a uniform gate insulating film with low interface state density can be formed. A transistor whose gate insulating film partially or wholly includes an insulating film formed by high-density plasma treatment can have suppressed variations in characteristics.

Next, as shown in FIG. 15C, a conductive film is formed over the gate insulating film 710, and the conductive film is patterned into predetermined shapes, so that gate electrodes 711 are formed above the island-shaped semiconductor films 705 to 709. In this embodiment, the gate electrodes 711 are each formed by patterning two stacked conductive films. For the conductive films, metals such as tantalum (Ta), tungsten (W), titanium (Ti), molybdenum (Mo), aluminum (Al), copper (Cu), chromium (Cr), and niobium (Nb) can be used. Alternatively, an alloy containing the above-described metal as a main component or a compound containing the above-described metal can also be used. Further, it is also possible to use a semiconductor, e.g., polycrystalline silicon doped with an impurity element such as phosphorus which imparts one conductivity type to the semiconductor film.

In this embodiment, a tantalum nitride film or a tantalum (Ta) film is used as a first conductive film, and a tungsten (W) film is used as a second conductive film. Besides the example shown in this embodiment, the following combinations of two conductive films can be given as alternative examples: a tungsten nitride film and a tungsten film, a molybdenum nitride film and a molybdenum film, an aluminum film and a tantalum film, an aluminum film and a titanium film, and the like. Tungsten and tantalum nitride have high heat resistance. Therefore, after the formation of the two conductive films, they may be heated for the purpose of thermal activation. Further, as other exemplary combinations of two conductive films, it is also possible to use silicon doped with an n-type impurity and nickel silicide, silicon doped with an n-type impurity and tungsten silicide, and the like.

Although this embodiment illustrates the gate electrode 711 having two stacked conductive films, the invention is not limited to this structure. The gate electrode 711 may also be formed from a single conductive film or more than two stacked conductive films. In the case of using a three-layer structure in which more than two conductive films are stacked, it is preferable to form a stacked structure of a molybdenum film, an aluminum film, and a molybdenum film.

The conductive films can be formed by a CVD method, a sputtering method, or the like. In this embodiment, a first conductive film is formed to a thickness of 20 to 100 nm and a second conductive film is formed to a thickness of 100 to 400 nm.

Note that a resist mask used for the formation of the gate electrode 711 may be replaced with a mask made of silicon oxide, silicon oxynitride, or the like. In that case, it is necessary to perform an additional patterning step for formation of a mask of silicon oxide, silicon oxynitride, or the like. However, since reduction in thickness of the mask in etching is less than the case of using a resist, the gate electrode 711 with a desired width can be formed. Alternatively, the gate electrode 711 can be selectively formed by a droplet discharge method without using a mask.

Note that a droplet discharge method means a method of forming a predetermined pattern by discharging or ejecting a droplet containing a predetermined composition from an orifice. An inkjet method is given as one example.

Next, the island-shaped semiconductor films 705 to 709 are doped with an element which imparts n-type conductivity (typically, P (Phosphorus) or As (Arsenic)) with the gate electrodes 711 as masks, so that the island-shaped semiconductor films 705 to 709 contain the impurity element at a low concentration (a first doping step). The conditions of the first doping step are as follows: a dosage of $1\times10^{15}$ to $1\times10^{19}/cm^3$ and an acceleration voltage of 50 to 70 keV. However, the invention is not limited to such conditions. By this first doping step, doping is performed through the gate insulating film 710, so that a pair of n-type low concentration impurity regions 712 are formed in each of the island-shaped semiconductor films 705 to 709. Note that the first doping step may be performed with the island-shaped semiconductor film 708, which is to be a p-channel TFT, covered with a mask.

Next, as shown in FIG. 15D, a mask 770 is formed so as to cover the island-shaped semiconductor films 705 to 707 and 709 that are to be n-channel TFTs. Then, the island-shaped semiconductor film 708 is doped with an impurity element which imparts p-type conductivity (typically, B (boron)) with the mask 770 and the gate electrode 711 as masks, so that the island-shaped semiconductor film 708 contains the impurity element at a high concentration (a second doping step). The conditions of the second doping step are as follows: a dosage of $1\times10^{19}$ to $1\times10^{20}/cm^3$ and an acceleration voltage of 20 to 40 keV. By this second doping step, doping is performed through the gate insulating film 710, so that a pair of p-type high concentration impurity regions 713 are formed in the island-shaped semiconductor film 708.

Next, as shown in FIG. 16A, the mask 770 is removed by ashing or the like, and an insulating film is formed so as to cover the gate insulating film 710 and the gate electrodes 711. The insulating film is formed by depositing a silicon film, a silicon oxide film, a silicon oxynitride film, a silicon nitride oxide film, or a film containing an organic material such as an organic resin, either in a single layer or stacked layers by a plasma CVD method, a sputtering method, or the like. In this embodiment, a silicon oxide film is formed to a thickness of 100 nm by a plasma CVD method.

Next, the gate insulating film 710 and the insulating film are partially etched by anisotropic etching (mainly in the perpendicular direction). By this anisotropic etching, the gate insulating film 710 is partially etched to leave gate insulating films 714 that are partially formed over the island-shaped semiconductor films 705 to 709. In addition, the insulating film is also etched partially by the anisotropic etching, so that sidewalls 715 having a contact with the side faces of the gate electrodes 711 are formed. The sidewalls 715 are used as doping masks for formation of LDD (Lightly Doped Drain) regions. In this embodiment, a mixed gas of $CHF_3$ and He is used as an etching gas. Note that the step of forming the sidewalls 715 is not limited to this example.

Next, a mask is formed so as to cover the island-shaped semiconductor film 708 that is to be a p-channel TFT. Then, the island-shaped semiconductor films 705 to 707 and 709 are doped with an impurity element which imparts n-type conductivity (typically, P or As) by using the mask, the gate electrodes 711, and the sidewalls 715 as masks, so that the island-shaped semiconductor films 705 to 707 and 709 contain the impurity element at a high concentration (a third doping step). The conditions of the third doping step are as follows: a dosage of $1\times10^{19}$ to $1\times10^{20}/cm^3$ and an acceleration voltage of 60 to 100 keV. By this third doping step, a pair of n-type high concentration impurity regions 716 are formed in each of the island-shaped semiconductor films 705 to 707 and 709.

Note that the sidewalls 715 function as masks later at the time of forming low concentration impurity regions or non-doped offset regions below the sidewalls 715 by doping the semiconductor film with an impurity which imparts n-type conductivity so that the semiconductor film contains the impurity element at a high concentration. Therefore, in order to control the width of the low concentration impurity regions or the non-doped offset regions, the size of the sidewalls 715 may be controlled by appropriately changing the anisotropic etching conditions for the formation of the sidewalls 715 or the thickness of the insulating film.

Next, the mask is removed by ashing or the like, and then the impurity regions may be activated by thermal treatment. For example, a silicon oxynitride film with a thickness of 50 nm may be formed first, followed by thermal treatment at 550° C. in a nitrogen atmosphere for four hours.

Alternatively, a silicon nitride film containing hydrogen may be formed first to a thickness of 100 nm, followed by thermal treatment at 410° C. in a nitrogen atmosphere for one hour so that the island-shaped semiconductor films 705 to 709 are hydrogenated. As a further alternative, the island-shaped semiconductor films 705 to 709 may be subjected to thermal treatment at 300 to 450° C. in an atmosphere containing hydrogen for one to 12 hours so as to be hydrogenated. The thermal treatment can be performed by a thermal annealing method, a laser annealing method, an RTA method, or the like. By the thermal treatment, not only hydrogenation but also activation of the impurity element that has been added into the semiconductor films can be accomplished. As an alternative method of hydrogenation, it is also possible to perform plasma hydrogenation (which uses hydrogen excited by plasma). By such hydrogenation step, dangling bonds can be terminated with thermally excited hydrogen.

By the series of the above-described steps, n-channel TFTs 717 to 720 and a p-channel TFT 721 are formed.

Next, as shown in FIG. 16B, an insulating film 722 functioning as a passivation film is formed for protection of the TFTs 717 to 721. Although the insulating film 722 is not necessarily required, the provision of the insulating film 722 can prevent intrusion of an impurity such as an alkali metal or an alkaline earth metal into the TFTs 717 to 721. Specifically, it is preferable to use silicon nitride, silicon nitride oxide, aluminum nitride, aluminum oxide, silicon oxide, silicon oxynitride or the like for the insulating film 722. In this embodiment, a silicon oxynitride film with a thickness of about 600 nm is used for the insulating film 722. In this case, the above-described hydrogenation step may be performed after the formation of this silicon oxynitride film.

Next, an insulating film 723 is formed over the insulating film 722 so as to cover the TFTs 717 to 721. For the insulating film 723, thermally stable organic materials such as polyimide, acrylic, benzocyclobutene, polyamide, or epoxy can be used. In addition to such organic materials, it is also possible to use a low-dielectric constant material (a low-k material), a siloxane resin, silicon oxide, silicon nitride, silicon oxynitride, silicon nitride oxide, PSG (phosphosilicate glass), BPSG (borophosphosilicate), alumina, and the like. A siloxane resin may contain as a substituent at least one of fluorine, an alkyl group, and aromatic hydrocarbon, in addition to hydrogen. Note that the insulating film 723 can also be formed by stacking a plurality of insulating films made of such materials.

A method for forming the insulating film 723 can be selected as appropriate according to a material used, e.g., a CVD method, a sputtering method, a SOG method, spin coating, dipping, spray coating, a droplet discharge method (e.g., an inkjet method, screen printing, offset printing, or the like), a doctor knife, a roll coater, a curtain coater, a knife coater, or the like.

Next, contact holes are formed in the insulating films 722 and 723 so as to partially expose the island-shaped semiconductor films 705 to 709. Then, conductive films 724 to 733 are formed so as to be in contact with the island-shaped semiconductor films 705 to 709 through the contact holes. Although a mixed gas of $CHF_3$ and He is used as an etching gas for formation of the contact holes, the invention is not limited to this.

The conductive films 724 to 733 can be formed by a CVD method, a sputtering method, or the like. Specifically, the conductive films 724 to 733 can be formed using aluminum (Al), tungsten (W), titanium (Ti), tantalum (Ta), molybdenum (Mo), nickel (Ni), platinum (Pt), copper (Cu), gold (Au), silver (Ag), manganese (Mn), neodymium (Nd), carbon (C), silicon (Si), or the like. Alternatively, an alloy containing the above-described metal as a main component or a compound containing the above-described metal can also be used. The conductive films 724 to 733 can be either a single layer of the above-described metal film or a plurality of stacked layers thereof.

As an example of an alloy containing aluminum as a main component, an alloy which contains aluminum as a main component and contains nickel can be given. Further, an alloy which contains aluminum as a main component and contains nickel and one or both of carbon and silicon can also be given. Aluminum and aluminum silicon, which have a low resistance value and are inexpensive, are the most suitable materials for formation of the conductive films 724 to 733. In particular, when an aluminum silicon (Al—Si) film is used, generation of hillocks in resist baking can be suppressed more than the case of using an aluminum film, in patterning the conductive films 724 to 733. Further, instead of silicon (Si), about 0.5% Cu may be mixed into the aluminum film.

Each of the conductive films 724 to 733 is preferably formed to have a stacked structure of, for example, a barrier film, an aluminum silicon (Al—Si) film, and a barrier film, or a stacked structure of a barrier film, an aluminum silicon (Al—Si) film, a titanium nitride film, and a barrier film. Note that a barrier film is, for example, a film formed from titanium, titanium nitride, molybdenum, molybdenum nitride, or the like. When barrier films are formed to sandwich an aluminum silicon (Al—Si) film therebetween, generation of hillocks of aluminum or aluminum silicon can be prevented more effectively. In addition, when a barrier film made of titanium which is a high reducible element is formed, even when there are thin oxide films on the island-shaped semiconductor films 705 to 709, the oxide films can be reduced by titanium contained in the barrier film, whereby a favorable contact between the conductive films 724 to 733 and the island-shaped semiconductor films 705 to 709 can be obtained. Further, it is also possible to stack a plurality of barrier films In that case, the conductive films 724 to 733 can each have a five-layer structure in which titanium, titanium nitride, aluminum silicon, titanium, and titanium nitride are sequentially stacked.

Note that the conductive films 724 and 725 are connected to the high concentration impurity regions 716 of the n-channel TFT 717. The conductive films 726 and 727 are connected to the high concentration impurity regions 716 of the n-channel TFT 718. The conductive films 728 and 729 are connected to the high concentration impurity regions 716 of the n-channel TFT 719. The conductive films 730 and 731 are connected to the high concentration impurity regions 713 of the p-channel TFT 721. The conductive films 732 and 733 are connected to the high concentration impurity regions 716 of the n-channel TFT 720.

Next, as shown in FIG. 16C, an insulating film 734 is formed so as to cover the conductive films 724 to 733. Then, contact holes are formed in the insulating film 734 so as to partially expose the conductive films 724, 726, 728, and 733. Then, conductive films 735 to 738 are formed so as to be in contact with the conductive films 724, 726, 728, and 733, respectively at the contact holes. Any material that can be used for the conductive films 724 to 733 can be used as the material of the conductive films 735 to 738.

The insulating film 734 can be formed using an organic resin film, an inorganic insulating film, or a siloxane insulating film. Examples of an organic resin film include acrylic, epoxy, polyimide, polyamide, polyvinyl phenol, benzocyclobutene, and the like. Examples of an inorganic insulating film include silicon oxide, silicon oxynitride, silicon nitride oxide, a film containing carbon typified by DLC (diamond-like carbon), and the like. Note that a mask used for formation of an opening through a photolithography method can be formed by a droplet discharge method or a printing method. A method of forming the insulating film 734 can be selected as appropriate according to a material used, e.g., a CVD method, a sputtering method, a droplet discharge method, a printing method, or the like.

Next, a conductive film 739 functioning as an antenna and conductive films 740 to 742 functioning as wires are formed so as to be in contact with the conductive films 735 to 738. In this embodiment, the conductive films 737 and 739 are in contact. Similarly, the conductive films 735 and 740 are in contact, the conductive films 736 and 741 are in contract, and the conductive films 738 and 742 are in contact.

The conductive films 739 to 742 can be formed using a metal such as silver (Ag), gold (Au), copper (Cu), palladium (Pd), chromium (Cr), platinum (Pt), molybdenum (Mo), titanium (Ti), tantalum (Ta), tungsten (W), aluminum (Al), iron (Fe), cobalt (Co), zinc (Zn), tin (Sn), or nickel (Ni). In addition to such metal films, the conductive films 739 to 742 can also be formed using a film made of an alloy containing the above-described metal as a main component or a compound containing the above-described metal. The conductive films 739 to 742 can be either a single layer of the above-described film or a plurality of stacked layers thereof.

The conductive films 739 to 742 can be formed by a CVD method, a sputtering method, a printing method such as screen printing or gravure printing, a droplet discharge method, a dispensing method, a plating method, a photolithography method, an evaporation method, or the like.

In the case of using a screen printing method, for example, the conductive films 739 to 742 can be formed by selectively printing a conductive paste, in which conductive particles with a particle size of several nm to several ten μm are dispersed in an organic resin, onto the insulating film 734. The conductive particles can be formed using silver (Ag), gold (Au), copper (Cu), nickel (Ni), platinum (Pt), palladium (Pd), tantalum (Ta), molybdenum (Mo), tin (Sn), lead (Pb), zinc (Zn), chromium (Cr), titanium (Ti), or the like. In addition to such metals, the conductive particles can also be formed using an alloy containing the above-described metal as a main component or a compound containing the above-described metal. Further, it is also possible to use fine particles of silver halide or dispersible nanoparticles. In addition, as an organic resin contained in the conductive paste, polyimide, a siloxane resin, an epoxy resin, a silicone resin, or the like can be used.

As exemplary alloys of the above-described metals, the following combinations can be given: silver (Ag) and palladium (Pd), silver (Ag) and platinum (Pt), gold (Au) and platinum (Pt), gold (Au) and palladium (Pd), and silver (Ag) and copper (Cu). Further, conductive particles of copper (Cu) coated with silver (Ag) can also be used, for example.

Note that the conductive films 739 to 742 are preferably formed by the steps of extruding a conductive paste by a printing method or a droplet discharge method, and baking the paste. For example, in the case of using conductive particles (e.g., a particle size of 1 to 100 nm) containing silver as a main component for the conductive paste, the conductive films 739 to 742 can be formed by baking the conductive paste at a temperature in the range of 150 to 300° C. Baking may be performed either by lamp annealing with an infrared lamp, a xenon lamp, a halogen lamp, or the like, or by furnace annealing with an electric furnace. Further, laser annealing with an excimer laser or an Nd:YAG laser may also be used. In addition, fine particles containing solder or lead-free solder as a main component can also be used. In that case, it is preferable to use fine particles with a particle size not greater than 20 μm. Solder and lead-free solder have the advantage of low cost.

When a printing method or a droplet discharge method is used, the conductive films 739 to 742 can be formed without using an exposure mask. Further, when a droplet discharge method or a printing method is used, waste of materials due to etching can be prevented unlike a photolithography method. Further, since an expensive exposure mask is not required, the fabrication cost of the wireless sensor device can be suppressed.

Figure 17A:
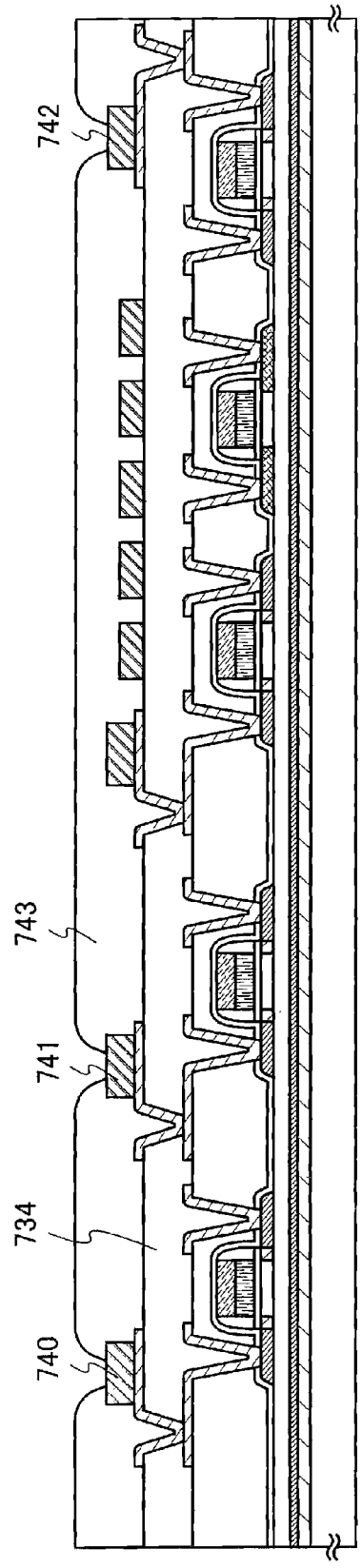
FIGS. 17A and 17B illustrate a method of fabricating a wireless sensor device of the invention.

Next, as shown in FIG. 17A, an insulating film 743 is formed over the insulating film 734 so as to cover the conductive films 739 to 742. Then, contact holes are formed in the insulating film 743 so as to partially expose the conductive films 740 to 742 functioning as the wires. The insulating film 743 can be formed using an organic resin film, an inorganic insulating film, or a siloxane insulating film. Examples of an organic resin film include acrylic, epoxy, polyimide, polyamide, polyvinyl phenol, benzocyclobutene, and the like. Examples of an inorganic insulating film include silicon oxide, silicon oxynitride, silicon nitride oxide, a film containing carbon typified by DLC (diamond-like carbon), and the like. Note that a mask used for formation of an opening through a photolithography method can be formed by a droplet discharge method or a printing method. A method of forming the insulating film 743 can be selected as appropriate according to a material used, e.g., a CVD method, a sputtering method, a droplet discharge method, a printing method, or the like.

Figure 17B:
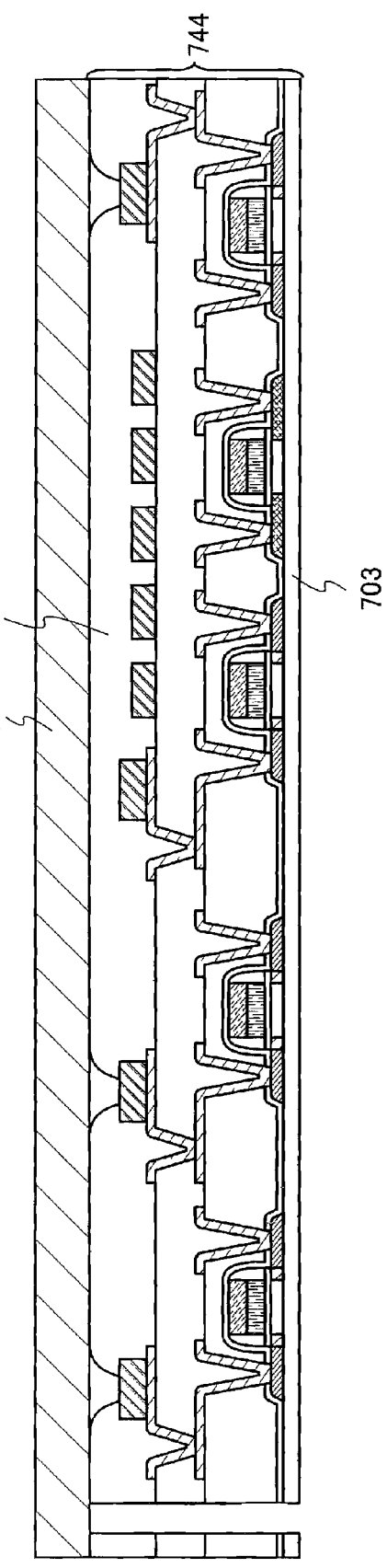

Next, as shown in FIG. 17B, layers of from the insulating film 703 up to the insulating film 743, which include semiconductor elements typified by TFTs and various conductive films, (hereinafter collectively referred to as an "element formation layer 744") are peeled off the substrate 700. In this embodiment, a first seat material 745 is bounded to a surface of the insulating film 743 of the element formation layer 744, and the element formation layer 744 is peeled off the substrate 700 by using a physical force. The release layer 702 may partially remain without being entirely removed.

The above-described peeling step may be performed by a method of etching the release layer 702. In this case, a protective layer is formed so as to cover the conductive films 740 to 742 in order to protect part of the conductive films 740 to 742 that has been exposed by etching. Then, a trench is formed so as to partially expose the release layer 702. The trench is formed by dicing, scribing, laser (including UV light) processing, a photolithography method, or the like. The trench may be deep enough to expose the release layer 702.

The protective layer can be formed with an epoxy resin, acrylate resin, a silicone resin, or the like that is soluble in water or alcohols. For example, the protective layer can be formed by the steps of applying a water-soluble resin (VL-WSHL10, product of Toagosei Co., Ltd.) to a thickness of 30 μm by a spin coating method, pre-curing the resin by light exposure for two minutes, and completely curing the resin by light exposure again for 12.5 minutes in total (2.5 minutes from the rear surface and 10 minutes from the front surface). In the case of stacking a plurality of organic resins, there is a possibility that part of the organic resins might be melted or adhesion thereof might become extremely high during a coating step or a baking step depending on a solvent used. Therefore, in the case of using organic resins that are soluble in the same solvent for the insulating film 743 and the protective layer, it is preferable to form an inorganic insulating film (e.g., a silicon nitride film, a silicon nitride oxide film, an aluminum nitride film, or an aluminum nitride oxide film) so as to cover the insulating film 743 in order that the protective layer can be smoothly removed in a subsequent step. After the formation of the protective layer, the release layer 702 is removed by etching. In this case, halogen fluoride is used as an etching gas, and the gas is introduced through the trench. In this embodiment, etching is performed under the conditions of, for example, using $ClF_3$ (chlorine trifluoride), a temperature of 350° C., a flow rate of 300 sccm, an atmospheric pressure of 6 Torr, and a period of three hours. In addition, nitrogen may be mixed into the $ClF_3$ gas. Using halogen fluoride such as $ClF_3$ enables the release layer 702 to be selectively etched, so that the substrate 700 can be peeled off the TFTs 717 to 721. Note that halogen fluoride may be either gas or liquid.

Next, as shown in FIG. 18A, a second seat material 746 is attached to a surface of the element formation layer 744 that is exposed by the above-described peeling step, and then the element formation layer 744 is peeled off the first seat material 745. Then, conductive films 747 to 749, which are connected to the conductive films 740 to 742, respectively through contact holes, are formed. In this embodiment, the conductive films 740 and 747 are in contact, the conductive films 741 and 748 are in contact, and the conductive films 742 and 749 are in contact.

The conductive films 747 to 749 can be formed using metals such as silver (Ag), gold (Au), copper (Cu), palladium (Pd), chromium (Cr), platinum (Pt), molybdenum (Mo), titanium (Ti), tantalum (Ta), tungsten (W), aluminum (Al), iron (Fe), cobalt (Co), zinc (Zn), tin (Sn), and nickel (Ni). In addition to such metal films, the conductive films 747 to 749 can also be formed using a film made of an alloy containing the above-described metal as a main component or a compound containing the above-described metal. The conductive films 747 to 749 can be either a single layer of the above-described film or a plurality of stacked layers thereof.

The conductive films 747 to 749 can be formed by a CVD method, a sputtering method, a printing method such as screen printing or gravure printing, a droplet discharge method, a dispensing method, a plating method, a photolithography method, an evaporation method, or the like.

Although this embodiment illustrates an example where the conductive films 747 to 749 are formed after peeling the element formation layer 744 off the substrate 733, the formation of the conductive films 747 to 749 may precede the peeling of the element formation layer 744 off the substrate 700.

Note that in the case where semiconductor elements corresponding to a plurality of wireless sensor devices are formed over the substrate 700, the element formation layer 744 is cut into individual wireless sensor devices. Cutting can be performed with a laser irradiation apparatus, a dicing apparatus, a scribing apparatus, or the like. In this embodiment, a plurality of semiconductor elements formed over one substrate 700 are cut into corresponding wireless sensor devices by laser irradiation.

Next, a substrate 751 having a battery and a terminal for connecting a sensor to a semiconductor element is prepared. This embodiment illustrates an example where a thin-film secondary battery 750 shown in Embodiment 5 is used as a battery as shown in FIG. 18B.

Next, the structures of the thin-film secondary battery 750 and the terminal shown in FIG. 18B will be described. First, conductive films 752 and 753 are formed over the substrate 751. The conductive film 752 functions as a terminal for connecting a sensor to a semiconductor element. The thin-film secondary battery 750 is formed over the substrate 751. Specifically, the thin-film secondary battery 750 has a structure in which a current-collecting thin film 754 connected to the conductive film 753, a negative electrode active material layer 755, a solid electrolyte layer 756, a positive electrode active material layer 757, and a current-collecting thin film 758 are sequentially stacked over the substrate 751.

The current-collecting thin film 754 should have high adhesion to the negative electrode active material layer 755 and have low resistance. For example, aluminum, copper, nickel, vanadium, gold, or the like is preferably used for the current-collecting thin film 754. For the negative electrode active material layer 755, vanadium oxide or the like is generally used. For the solid electrolyte layer 756, lithium phosphate, lithium phosphate doped with nitrogen, or the like is generally used. For the positive electrode active material layer 757, lithium manganate or the like is generally used. It is also possible to use lithium cobaltate or lithium nickel oxide for the positive electrode active material layer 757. The current-collecting thin film 758 should have high adhesion to the positive electrode active material layer 757 and have low resistance. For example, aluminum, copper, nickel, vanadium, gold, or the like can be used. Alternatively, the current-collecting thin film 754 or 758 may also be formed using a light-transmissive conductive material such as ITO (Indium Tin Oxide).

Each of the above-described thin layers of the negative electrode active material layer 755, the solid electrolyte layer 756, the positive electrode active material layer 757, and the current-collecting thin film 758 may be formed by using either a sputtering method or an evaporation method. In addition, the thickness of each layer is preferably 0.1 to 3 µm.

Next, an interlayer film 759 is formed using a resin. Then, the interlayer film 759 is etched to form contact holes. The material of the interlayer film 759 is not limited to a resin, and another film such as a CVD oxide film may also be used. However, using a resin is preferable in terms of flatness. Further, a photosensitive resin may also be used so that contact holes can be formed in the interlayer film 759 without etching. Next, conductive films 760 to 762 are formed over the interlayer film 759. The conductive film 760 is in contact with the conductive film 752 through the contact hole. The conductive film 761 is in contact with the current-collecting thin film 758 through the contact hole. By electrically connecting the conductive film 762 to the conductive film 753, electrical connection of the thin-film secondary battery 750 can be secured.

The conductive film 752 is connected to a conductive film 763 that is formed on an opposite surface (a second surface) to a surface (a first surface) of the substrate 751 having the conductive film 752, through a contact hole formed in the substrate 751. The contact hole in the substrate 751 may be formed by etching or laser ablation. In order to facilitate the formation of the contact hole, the substrate 751 may be polished and thinned by a CMP (Chemical-Mechanical Polishing) method after the formation of the conductive films 760 to 762. In this embodiment, the conductive film 763 and the wire 764 connected to the sensor are electrically connected.

Figure 19:
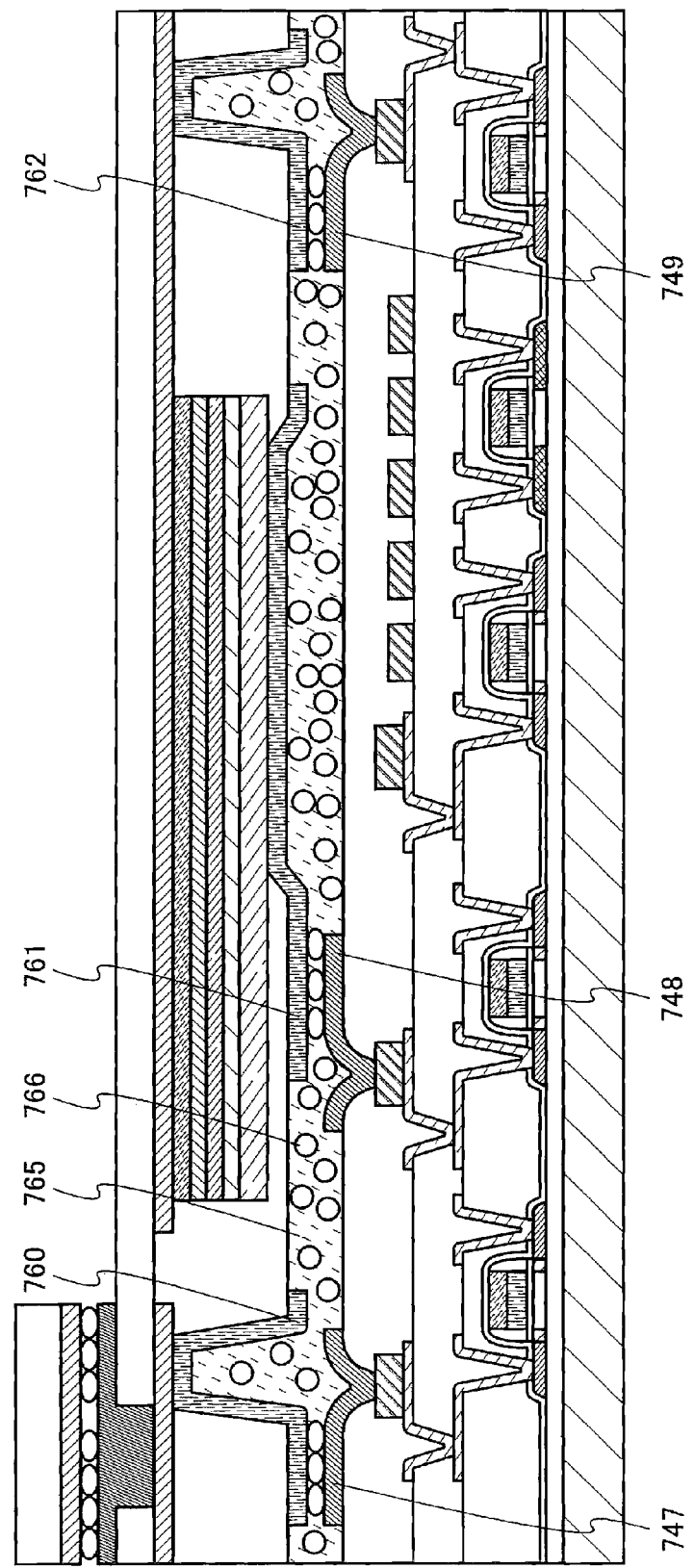
FIG. 19 illustrates a method of fabricating a wireless sensor device of the invention.

Next, as shown in FIG. 19, the conductive films 747 to 749 provided on the element formation layer 744 and the conductive films 760 to 762 are electrically connected. Specifically, the conductive film 747 and the conductive film 760 are electrically connected. In addition, the conductive film 748 and the conductive film 761 are electrically connected, and also the conductive film 749 and the conductive film 762 are electrically connected.

This embodiment illustrates the case where the conductive films 747 to 749 and the conductive films 760 to 762 are electrically connected by pressure bonding with an anisotropic conductive film (ACF), an anisotropic conductive paste (ACP), or the like. In this embodiment, an example is shown in which connection is carried out with conductive particles 766 in an adhesive resin 765. Alternatively, connection may also be carried out with a conductive adhesive such as a silver paste, a copper paste, or a carbon paste, soldering, or the like.

Note that it is also possible to attach a third sheet material over the substrate 751 having the thin-film secondary battery 750 and the sensor electrically connected to the conductive film 752, so that the second seat material 746 and the third sheet material are bonded through one or both of thermal treatment and pressure treatment. As the second sheet material 746 and the third sheet material, hot-melt films and the like can be used.

For the second sheet material 746 and the third sheet material, it is possible to use a film on which antistatic treatment for preventing static electricity or the like has been applied (hereinafter referred to as an antistatic film). By sealing the device with antistatic films, semiconductor elements can be prevented from adverse effects such as external static electricity when dealt with as a commercial product.

Examples of an antistatic film include a film in which a material that can prevent electrostatic charge (an antistatic material) is mixed, a film having an antistatic effect, a film coated with an antistatic agent, and the like. As an antistatic agent, the following can be used: nonionic polymers, anionic polymers, cationic polymers, a nonionic surfactant, an anionic surfactant, a cationic surfactant, or an amphoteric surfactant. Alternatively, metals, indium tin oxide (ITO), or the like can also be used as the antistatic agent. Exemplary materials of a film having an antistatic effect include an olefin resin, an ABS resin, a styrene resin, a PMMA resin, a polycarbonate resin, a PVC polyester resin, a polyamide resin, a modified PPO resin, and the like.

Although this embodiment has illustrated the example where a sensor which is separately prepared is electrically connected to the semiconductor elements included in the element formation layer 744, the invention is not limited to this structure. For example, the sensor may be formed over the same substrate 700 as the semiconductor elements.

Figure 23:
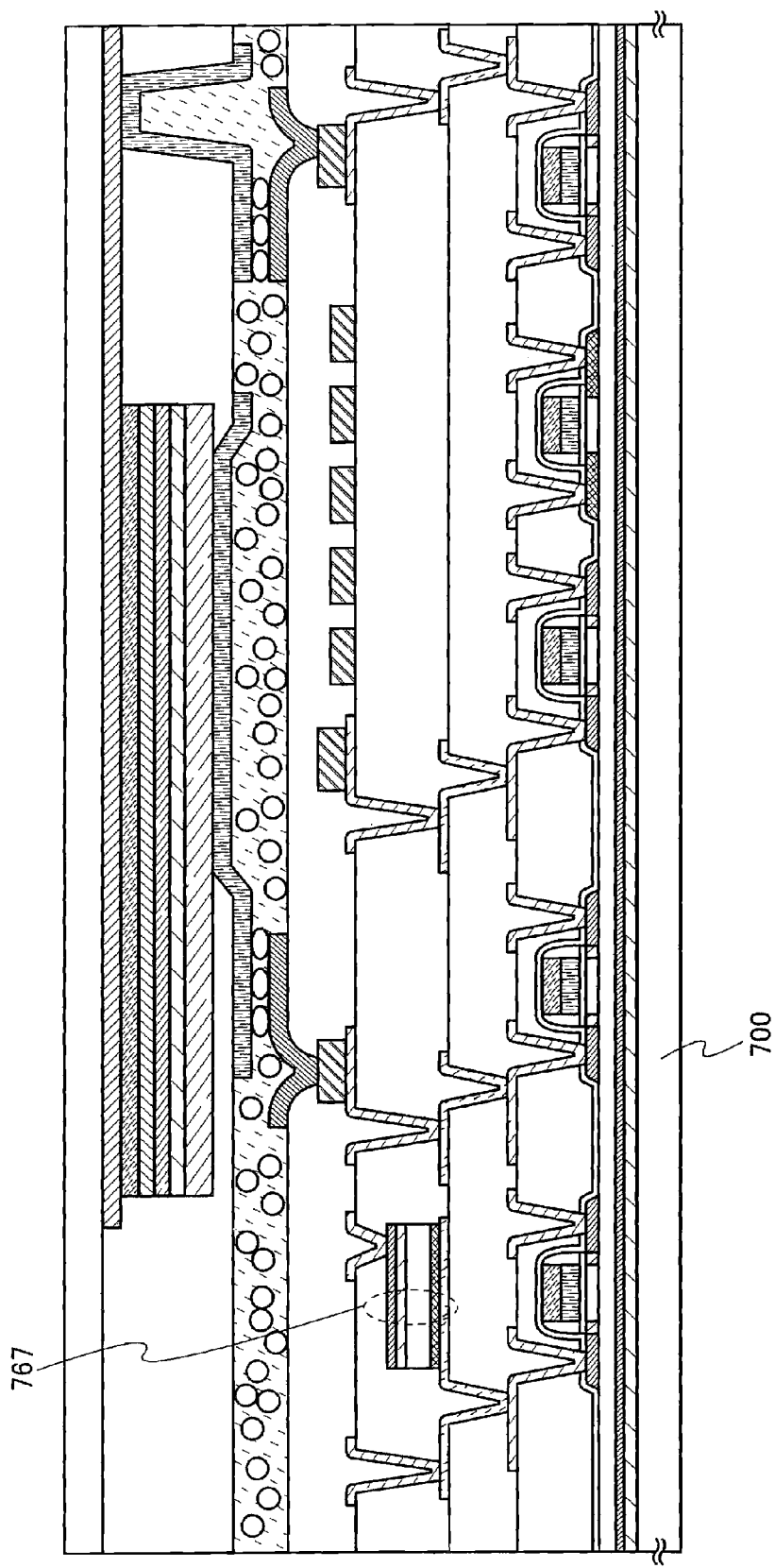
FIG. 23 illustrates the configuration of a wireless sensor device of the invention.

FIG. 23 illustrates the structure of the wireless sensor device of the invention in which a photoelectric conversion element 767 is formed over the substrate 700. Note that a sensor is not limited to the photoelectric conversion element, and any of a resistor, an element which uses capacitive coupling, an element which uses induced electromotive force, a photovoltaic element, a thermoelectric conversion element, a transistor, a thermistor, a diode, and the like can be used.

Note that this embodiment can be implemented in combination with any of Embodiment Modes 1 to 3 and Embodiments 1 to 8.

Embodiment 10

This embodiment will describe an example where the wireless sensor device of the invention is fabricated with transistors formed on a single-crystalline substrate. Since transistors formed on a single-crystalline substrate have small variations in characteristics, the number of transistors used for the wireless sensor device can be suppressed. In addition, this embodiment illustrates an example where a thin-film secondary battery described in Embodiment 5 is used as a battery.

First, as shown in FIG. 20A, element-isolation insulating films 2301 for electrically insulating semiconductor elements are formed using insulating films, over a semiconductor substrate 2300. The formation of the element-isolation insulating films 2301 allows a region 2302 for formation of transistors (an element formation region) and an element formation region 2303 to be electrically insulated from each other.

The semiconductor substrate 2300 can be, for example, a single-crystalline silicon substrate having n-type or p-type conductivity, a compound semiconductor substrate (e.g., a GaAs substrate, an InP substrate, a GaN substrate, a SiC substrate, a sapphire substrate, or a ZnSe substrate), or the like.

The element-isolation insulating film 2301 can be formed by a LOCOS (LOCal Oxidation of Silicon) method, a trench isolation method, or the like.

In this embodiment, an example is shown in which a single-crystalline silicon substrate having n-type conductivity is used as the semiconductor substrate 2300, and a p-well 2304 is formed in the element formation region 2303. The p-well 2304 formed in the element formation region 2303 of the semiconductor substrate 2300 can be formed by selectively doping the element formation region 2303 with an impurity element which imparts p-type conductivity. As the impurity element which imparts p-type conductivity, boron (B), aluminum (Al), gallium (Ga), or the like can be used. In the case of using a semiconductor substrate having p-type conductivity as the substrate 2300, an n-well region may be formed by selectively doping the element formation region 2302 with an impurity element which imparts n-type conductivity.

Note that in this embodiment, the element formation region 2302 is not doped with an impurity element because a semiconductor substrate having n-type conductivity is used as the semiconductor substrate 2300. However, an n-well region may be formed in the element formation region 2302 by doping the element formation region 2302 with an impurity element which imparts n-type conductivity. As the impurity element which imparts n-type conductivity, phosphorus (P), arsenic (As), or the like can be used.

Next, as shown in FIG. 20B, insulating films 2305 and 2306 are formed so as to cover the element formation regions 2302 and 2303, respectively. In this embodiment, silicon oxide films formed in the element formation regions 2302 and 2303 by thermally oxidizing the semiconductor substrate 2300 are used as the insulating films 2305 and 2306. Alternatively, it is also possible to use stacked layers of a silicon oxide film and a silicon oxynitride film, which are obtained by sequentially forming a silicon oxide film by thermal oxidation and forming a silicon oxynitride film thereon by nitriding the surface of the silicon oxide film by nitridation treatment, for the insulating films 2305 and 2306.

Further, as has been previously described, the insulating films 2305 and 2306 may also be formed by plasma treatment. For example, by oxidizing or nitriding the surface of the semiconductor substrate 2300 by high-density plasma treatment, silicon oxide films or silicon nitride films to be used as the insulating films 2305 and 2306 can be formed in the element formation regions 2302 and 2303, respectively.

Next, as shown in FIG. 20C, a conductive film is formed so as to cover the insulating films 2305 and 2306. In this embodiment, an example is shown in which conductive films 2307 and 2308 that are sequentially stacked are used. The conductive film may be either a single layer or a stacked structure of more than two conductive films.

For the conductive films 2307 and 2308, metals such as tantalum (Ta), tungsten (W), titanium (Ti), molybdenum (Mo), aluminum (Al), copper (Cu), chromium (Cr), and niobium (Nb) can be used. In addition to such metal films, the conductive films 2307 and 2308 can also be formed using a film made of an alloy containing the above-described metal as a main component or a compound containing the above-described metal. Further, it is also possible to use a semiconductor, e.g., polycrystalline silicon doped with an impurity element such as phosphorus which imparts one conductivity type to the semiconductor film. In this embodiment, the conductive film 2307 is formed using tantalum nitride and the conductive film 2308 is formed using tungsten.

Next, as shown in FIG. 21A, the stacked conductive films 2307 and 2308 are patterned into predetermined shapes, whereby gate electrodes 2309 and 2310 are formed over the insulating films 2305 and 2306, respectively.

Next, as shown in FIG. 21B, a resist mask 2311 is selectively formed so as to cover the element formation region 2302. Then, the element formation region 2303 is doped with an impurity element. In doping the element formation region 2303 with the impurity element, the gate electrode 2310 as well as the mask 2311 functions as a mask. Therefore, impurity regions 2312 functioning as source and drain regions and a channel formation region 2313 are formed in the p-well 2304. As the impurity element, an impurity element which imparts n-type conductivity or p-type conductivity is used. As the impurity element which imparts n-type conductivity, phosphorus (P), arsenic (As), or the like can be used. As the impurity element which imparts p-type conductivity, boron (B), aluminum (Al), gallium (Ga), or the like can be used. In this embodiment, phosphorus (P) is used as the impurity element.

Next, the mask 2311 is removed, and a resist mask 2314 is selectively formed so as to cover the element formation region 2303, as shown in FIG. 21C. Then, the element formation region 2302 is doped with an impurity element. In doping the element formation region 2302 with the impurity element, the gate electrode 2309 as well as the mask 2314 functions as a mask. Therefore, impurity regions 2315 functioning as source and drain regions and a channel formation region 2316 are formed in the element formation region 2302 of the semiconductor substrate 2300. As the impurity element, an impurity element which imparts n-type conductivity or p-type conductivity is used. As the impurity element which imparts n-type conductivity, phosphorus (P), arsenic (As), or the like can be used. As the impurity element which imparts p-type conductivity, boron (B), aluminum (Al), gallium (Ga), or the like can be used. In this embodiment, an impurity element (e.g., boron (B)) having a different conductivity type than the impurity element that has been added into the element formation region 2303 in FIG. 21B is used.

Next, as shown in FIG. 22A, an insulating film 2317 is formed so as to cover the insulating films 2305 and 2306 and the gate electrodes 2309 and 2310. Then, contact holes are formed in the insulating film 2317 to partially expose the impurity regions 2312 and 2315. Next, conductive films 2318 which are connected to the impurity regions 2312 and 2315 through the contact holes are formed. The conductive films 2318 can be formed by a CVD method, a sputtering method, or the like.

The insulating film 2317 can be formed using an inorganic insulating film, an organic resin film, or a siloxane insulating film. Examples of an inorganic insulating film include silicon oxide, silicon oxynitride, silicon nitride oxide, a film containing carbon typified by DLC (diamond-like carbon), and the like. Examples of an organic resin film include acrylic, epoxy, polyimide, polyamide, polyvinyl phenol, benzocyclobutene, and the like. A method of forming the insulating film 2317 can be selected as appropriate according to a material used, e.g., a CVD method, a sputtering method, a droplet discharge method, a printing method, or the like.

Note that the structure of the transistors used in the wireless sensor device of the invention is not limited to that shown in this embodiment. For example, an inversely staggered structure may be used.

Next, as shown in FIG. 22B, a thin-film secondary battery 2319 is formed. The thin-film secondary battery 2319 in this embodiment has a structure in which the conductive film 2318 serving as a current-collecting thin film, a negative electrode active material layer 2320, a solid electrolyte layer 2321, a positive electrode active material layer 2322, and a current-collecting thin film 2323 are sequentially stacked. Note that the conductive film 2318 should have high adhesion to the negative electrode active material layer 2320 and have low resistance, because part of the conductive film 2318 is used as the current-collecting thin film in this embodiment. The conductive film 2318 is preferably formed using aluminum, copper, nickel, vanadium, gold, or the like.

The structure of the thin-film secondary battery 2319 will now be described in detail. In the thin-film secondary battery 2319, the negative electrode active material layer 2320 is formed over the conductive film 2318. Generally, vanadium oxide or the like is used for the negative electrode active material layer 2320. Next, a solid electrolyte layer 2321 is formed over the negative electrode active material layer 2320. Generally, lithium phosphate, lithium phosphate doped with nitrogen, or the like is used. Next, the positive electrode active material layer 2322 is formed over the solid electrolyte layer 2321. Generally, lithium manganate or the like is used. Lithium cobaltate or lithium nickel oxide may also be used. Then, the current-collecting thin film 2323 to serve as an electrode is formed over the positive electrode active material layer 2322. The current-collecting thin film 2323 should have high adhesion to the positive electrode active material layer 2322 and have low resistance. For example, aluminum, copper, nickel, vanadium, gold, or the like can be used.

Alternatively, the conductive film 2318 or the current-collecting thin film 2323 may also be formed using a light-transmissive conductive material such as ITO (Indium Tin Oxide).

Each of the above-described thin layers of the negative electrode active material layer 2320, the solid electrolyte layer 2321, the positive electrode active material layer 2322, and the current-collecting thin film 2323 may be formed by using either a sputtering method or an evaporation method. In addition, the thickness of each layer is preferably 0.1 to 3 μm.

Next, an interlayer film 2324 is formed using a resin. Then, the interlayer film 2324 is etched to form contact holes. The material of the interlayer film is not limited to a resin, and another film such as a CVD oxide film may also be used. However, using a resin is preferable in terms of flatness. Further, a photosensitive resin may also be used so that contact holes can be formed without etching. Next, wire layers 2325 and 2326 are formed over the interlayer film. By connecting the wire layer 2325 and the conductive film 2318, electrical connection of the thin-film secondary battery 2319 is secured. Further, by connecting the wire layer 2326 and the conductive film 2318, a sensor can be electrically connected to the wire layer 2326.

Although this embodiment has illustrated the example where a sensor which is separately prepared is electrically connected to the wire layer 2326, the invention is not limited to this structure. For example, the sensor may be formed over the semiconductor substrate 2300. In this case, the sensor can be formed using any of a resistor, an element which uses capacitive coupling, an element which uses induced electromotive force, a photovoltaic element, a thermoelectric conversion element, a photoelectric conversion element, a transistor, a thermistor, a diode, and the like.

By using the above-described fabrication method, the wireless sensor device of the invention can have a structure in which a transistor is formed on a semiconductor substrate and a thin-film secondary battery is formed thereon. With such a structure, a wireless sensor device that is reduced in thickness and size can be provided.

Note that this embodiment can be implemented in combination with any of Embodiment Modes 1 to 3 and Embodiments 1 to 9.

The present application is based on Japanese Priority application No. 2006-263752 filed on Sep. 28, 2006 with the Japanese Patent Office, the entire contents of which are hereby incorporated by reference.

What is claimed is:

1. A wireless sensor device comprising:
   a semiconductor substrate;
   a circuit comprising a plurality of semiconductor elements, wherein the plurality of semiconductor elements are formed using the semiconductor substrate;
   a first insulating film covering the plurality of semiconductor elements;
   a thin-film secondary battery over the first insulating film;
   a second insulating film covering the thin-film secondary battery;
   a sensor electrically connected to the circuit through the first insulating film and the second insulating film;
   an antenna; and
   a package packing the semiconductor substrate, the circuit, the thin-film secondary battery, the sensor and the antenna.

2. The wireless sensor device according to claim 1, wherein the thin-film secondary battery is a thin-film lithium-ion secondary battery.

3. The wireless sensor device according to claim 1, wherein the thin-film secondary battery has a multi-layered structure, and
wherein each of layers forming the multi-layered structure has a thickness greater than or equal to 0.1 μm and less than or equal to 3 μm.

4. The wireless sensor device according to claim 1, wherein the circuit includes a rectifier circuit, a demodulation circuit, a modulation circuit and a logic circuit.

5. The wireless sensor device according to claim 1, wherein the wireless sensor device is used inside the living body.

6. The wireless sensor device according to claim 1, wherein a thickness of the wireless sensor device is less than or equal to 2 mm.

7. The wireless sensor device according to claim 1, wherein the sensor is one selected from the group consisting of a photoelectric conversion element, a resistor, an element which uses capacitive coupling, an element which uses induced electromotive force, a photovoltaic element, a thermoelectric conversion element, a transistor, a thermistor, and a diode.

8. A wireless sensor device comprising:
a first substrate;
a second substrate;
a thin-film secondary battery provided on a first surface of the first substrate;
a circuit provided on a first surface of the second substrate, the circuit comprising a plurality of semiconductor elements;
an insulating film covering the plurality of semiconductor elements;
an antenna over the insulating film;
a sensor electrically connected to the thin-film secondary battery and the circuit; and
a package packing the first substrate, the second substrate, the thin-film secondary battery, the circuit, the sensor and the antenna,
wherein the first surface of the first substrate and the first surface of the second substrate face each other, and
wherein the sensor is provided between the first substrate and the second substrate.

9. The wireless sensor device according to claim 8, wherein the thin-film secondary battery is a thin-film lithium-ion secondary battery.

10. The wireless sensor device according to claim 8,
wherein the thin-film secondary battery has a multi-layered structure, and
wherein each of layers forming the multi-layered structure has a thickness greater than or equal to 0.1 μm and less than or equal to 3 μm.

11. The wireless sensor device according to claim 8, wherein the circuit includes a rectifier circuit, a demodulation circuit, a modulation circuit and a logic circuit.

12. The wireless sensor device according to claim 8, wherein the wireless sensor device is used inside the living body.

13. The wireless sensor device according to claim 8, wherein a thickness of the wireless sensor device is less than or equal to 2 mm.

14. The wireless sensor device according to claim 8, wherein the sensor is one selected from the group consisting of a photoelectric conversion element, a resistor, an element which uses capacitive coupling, an element which uses induced electromotive force, a photovoltaic element, a thermoelectric conversion element, a transistor, a thermistor, and a diode.

15. A wireless sensor device comprising:
a first substrate;
a second substrate;
a thin-film secondary battery provided on a first surface of the first substrate;
a circuit provided on a first surface of the second substrate, the circuit comprising a plurality of semiconductor elements;
an insulating film covering the plurality of semiconductor elements;
an antenna over the insulating film;
a sensor attached to a second surface of the first substrate, the sensor electrically connected to the thin-film secondary battery and the circuit through the first substrate; and
a package packing the first substrate, the second substrate, the thin-film secondary battery, the circuit, the sensor and the antenna,
wherein the first surface of the first substrate and the first surface of the second substrate face each other.

16. The wireless sensor device according to claim 15, wherein the thin-film secondary battery is a thin-film lithium-ion secondary battery.

17. The wireless sensor device according to claim 15,
wherein the thin-film secondary battery has a multi-layered structure, and
wherein each of layers forming the multi-layered structure has a thickness greater than or equal to 0.1 μm and less than or equal to 3 μm.

18. The wireless sensor device according to claim 15, wherein the circuit includes a rectifier circuit, a demodulation circuit, a modulation circuit and a logic circuit.

19. The wireless sensor device according to claim 15, wherein the wireless sensor device is used inside the living body.

20. The wireless sensor device according to claim 15, wherein a thickness of the wireless sensor device is less than or equal to 2 mm.

21. The wireless sensor device according to claim 15, wherein the sensor is one selected from the group consisting of a photoelectric conversion element, a resistor, an element which uses capacitive coupling, an element which uses induced electromotive force, a photovoltaic element, a thermoelectric conversion element, a transistor, a thermistor, and a diode.

* * * * *

UNITED STATES PATENT AND TRADEMARK OFFICE
CERTIFICATE OF CORRECTION

PATENT NO. : 8,508,360 B2
APPLICATION NO. : 13/558373
DATED : August 13, 2013
INVENTOR(S) : Jun Koyama It is certified that error appears in the above-identified patent and that said Letters Patent is hereby corrected as shown below:

In the Specification

At column 11, line 5, "aluminuni" should be -- aluminum --;

At column 15, line 48, "film Accordingly," should be -- film. Accordingly, --;

At column 16, line 48, "nseo" should be -- nsec --.

Signed and Sealed this
Nineteenth Day of November, 2013

Teresa Stanek Rea
*Deputy Director of the United States Patent and Trademark Office*